United States Patent
Brik et al.

(10) Patent No.: US 11,806,098 B2
(45) Date of Patent: Nov. 7, 2023

(54) SURGICAL ROBOTIC SYSTEMS INCLUDING A STERILE CONNECTOR AND RELATED METHODS

(71) Applicant: DePuy Synthes Products, Inc., Raynham, MA (US)

(72) Inventors: Robert Brik, Cambridge, MA (US); William Frasier, New Bedford, MA (US); Tarik Yardibi, Wayland, MA (US); Brice Dudley, Jr., Round Rock, TX (US)

(73) Assignee: DePuy Synthes Products, Inc., Raynham, MA (US)

( * ) Notice: Subject to any disclaimer, the term of this patent is extended or adjusted under 35 U.S.C. 154(b) by 619 days.

(21) Appl. No.: 16/843,459

(22) Filed: Apr. 8, 2020

(65) Prior Publication Data

US 2021/0315646 A1    Oct. 14, 2021

(51) Int. Cl.
| | |
|---|---|
| *A61B 34/30* | (2016.01) |
| *A61B 34/00* | (2016.01) |
| *A61B 46/10* | (2016.01) |
| *A61B 17/14* | (2006.01) |
| *A61B 17/17* | (2006.01) |
| *A61B 17/92* | (2006.01) |
| *H01R 13/639* | (2006.01) |
| *A61B 17/00* | (2006.01) |

(52) U.S. Cl.
CPC ............ *A61B 34/30* (2016.02); *A61B 17/147* (2016.11); *A61B 17/17* (2013.01); *A61B 17/92* (2013.01); *A61B 34/25* (2016.02); *A61B 46/10* (2016.02); *H01R 13/639* (2013.01); *A61B 2017/00477* (2013.01); *A61B 2017/922* (2013.01); *H01R 2201/12* (2013.01)

(58) Field of Classification Search
CPC ..................................................... A61B 34/30
See application file for complete search history.

(56) References Cited

U.S. PATENT DOCUMENTS

| | | |
|---|---|---|
| 7,963,913 B2 | 6/2011 | Devengenzo et al. |
| 10,582,980 B2 | 3/2020 | Scheib et al. |

(Continued)

FOREIGN PATENT DOCUMENTS

| | | |
|---|---|---|
| GB | 2570518 A | 7/2019 |
| WO | WO 2017-205333 A1 | 11/2017 |

*Primary Examiner* — Sameh R Boles
(74) *Attorney, Agent, or Firm* — Condo Roccia Koptiw LLP

(57) ABSTRACT

Sterile connectors for robotic or robot-assisted surgery and related systems and methods can be used to establish a sterile barrier between a non-sterile robot arm and a surgical site. More particularly, a sterile connector can include a first component connector to couple to a distal end of a robot arm, a second component connector to couple to an end effector, and a sterile drape extending from the sterile connector. The sterile drape can drape the robot arm and can maintain a sterile barrier around the robot arm throughout the course of a surgical procedure. In this manner, an end effector can be swapped out during the procedure without the need to re-drape or re-establish the sterile surgical field. In some embodiments, the sterile connector can facilitate the passage of electrical signals and/or light between the sterile connector and at least one of the robot arm and end effector.

20 Claims, 21 Drawing Sheets

(56) References Cited

U.S. PATENT DOCUMENTS

2016/0242861 A1* 8/2016 Flatt ................. A61B 46/10
2018/0271616 A1   9/2018 Schuh et al.
2020/0022763 A1   1/2020 Hares et al.

* cited by examiner

SURGICAL ROBOTIC SYSTEMS INCLUDING A STERILE CONNECTOR AND RELATED METHODS

FIELD

Robotic surgical assemblies, including sterile connectors, and related methods are disclosed herein, e.g., for creating and maintaining a sterile barrier between a robot arm and a surgical site in association with a robotic or robot-assisted surgical procedure.

BACKGROUND

In a surgical operating room it can be important to maintain a sterile surgical field to reduce the risk of patient infection or other complications. To maintain sterility, any equipment that is to be used in the surgery must be sterilized before being brought into the sterile field, or must remain outside of the sterile field for the duration of a surgical procedure. With robotic or robot-assisted surgery, an increasing challenge can be effectively and efficiently maintaining sterility in a surgical procedure, which often can require at least a portion of a robot arm to enter a surgical site. The robot arm can be difficult and time-consuming to sterilize. Moreover, a robotic or robot-assisted surgical procedure can require changing or swapping out end effectors or surgical instruments coupled to the robot arm over the course of a surgical procedure. In such instances, the sterile field can be violated as a portion of the robot arm can become exposed.

In known surgical procedures, a robot arm can be covered with a sterile drape prior to a surgical procedure. In some instances, the robot arm can require re-draping whenever there is a change in an end effector or surgical tool used over the course of the procedure. This can be a time-consuming and cumbersome process. In other instances, a sterile drape can be coupled to an intermediate component that engages with a portion of the robot arm and an end effector. Such components, however, can inhibit communication and interaction between a user, the robot arm, and the end effector. Alternatively or in addition, use of such an intermediate component can require additional components to achieve a desired functionality (e.g., additional external electrical connections to enable a desired amount of power and/or electrical communication signals to be transmitted between the robot arm and the end effector).

Accordingly, there is a need for improved systems, methods, and devices for establishing and maintaining a sterile surgical field over the course of a robotic or robot-assisted surgical procedure in a reliable and less disruptive manner that can provide for additional operational capability and control.

SUMMARY

Robotic surgical systems including sterile connectors, and related methods, are disclosed herein for effectively and efficiently creating and maintaining a sterile barrier between a robot arm and a surgical site in a manner that does not disrupt flow of a surgical procedure or stymie communication and/or functional capabilities. The sterile connector can connect a distal end of a surgical robot arm to an end effector for use in a surgical procedure. A sterile drape can extend from the sterile connector and can establish a sterile barrier between the robot arm and a sterile surgical field for the duration of the surgical procedure. The robotic surgical systems disclosed herein can be designed such that the sterile connector cannot be removed from the robot arm while an end effector is coupled with the sterile connector. Accordingly, a risk that the sterile drape can be prematurely removed can be reduced. In some embodiments, the sterile connector can include one or more signal connectors that can be configured to pass at least one of electrical signals and light between the sterile connector and the robot arm and/or end effector.

In one aspect, a sterile connector can include a body, a sterile drape, and a signal connector. The body can have a first component connector that can be coupled to a surgical robot arm along a first axis and a second component connector that can be coupled to an end effector along a second axis. The first axis and the second axis can be transverse. The sterile drape can extend from the connector body. The signal connector can be disposed within the body and can be configured to transmit at least one of electrical signals and light between the sterile connector and at least one of the robot arm and the end effector.

The devices and methods described herein can have a number of additional features and/or variations, all of which are within the scope of the present disclosure. In some embodiments, for example, the first axis can be orthogonal to the second axis. Some embodiments can include a user interface on an outer surface of the connector body such that a user can access the user interface when the body is coupled to the surgical robot arm and the end effector.

In some embodiments, the first connector can be covered by the end effector when the sterile connector is coupled to the end effector. The first component connector can further include a lock that can be movable between a first position that locks the sterile connector to the robot arm and a second position that permits separation of the sterile connector and the robot arm. In some such embodiments, movement of the lock from the first position to the second position can be prohibited when the sterile connector is coupled to the end effector. In some instances, the sterile connector can extend radially through the body from an outer surface of the body towards a central longitudinal axis of the sterile connector. In other instances, the first component connector can extend through the body along a longitudinal axis of the connector.

The sterile connector can further include a second signal connector. The second signal connector can extend through the body and can be configured to transmit at least one of electrical signals and light between the sterile connector and at least one of the robot arm and the end effector. In some embodiments, the sterile drape can be sandwiched between a first portion of the body and a second portion of the body. The sterile drape can further include any of a conductive coating or a conductive thread.

In another aspect, a surgical method can include coupling a sterile connector to a distal end of a surgical robot arm along a first axis such that the sterile connector can extend distally from the robot arm along a longitudinal axis of the robot arm. The method can include locking the sterile connector to the robot arm and draping the robot arm with a sterile drape that can extend from a body of the sterile connector. Further, the method can conclude coupling an end effector to the sterile connector along a second axis and locking the end effector to the sterile connector. The first axis and the second axis can be transverse relative to one another and the longitudinal axis of the robot arm.

In some embodiments, coupling the sterile connector to the robot arm can further include radially inserting a first component connector of the sterile connector into a component connector of the robot arm. Coupling the end effector to the sterile connector can further include coupling the end effector to the sterile connector along an intended access of insertion of a surgical tool into a surgical site.

The method can further include passing at least one of electrical signals between the robot arm and the sterile connector, and, in some such embodiments, moving the robot arm through a user interface on an external surface of the sterile connector. The method can include passing at least one of electrical signals and light between the end effector and the sterile connector. In some such embodiments, the method can further include controlling a surgical instrument coupled to the end effector through a user interface on an external surface of the sterile connector.

In yet another aspect, a surgical method can include coupling a sterile connector to a distal end of a surgical robot arm by coupling a first component connector of the sterile connector with a component connector of the robot arm. The method can further include moving a first locking element of the first component connector of the sterile connector from an unlocked position to a locked position thereby locking the sterile connector to the robot arm, and draping the robot arm with a sterile drape extending from a body of the sterile connector to create a sterile barrier. The method can also include coupling an end effector to the sterile connector and locking the end effector to the sterile connector. Coupling the end effector to the sterile connector can prevent removal of the sterile connector from the robot arm.

Coupling the end effector to the sterile connector can prevent moving the first locking element from the locked position to the unlocked position. In some embodiments, attaching the end effector to the sterile connector can prevent access to the first locking element of the sterile connector. The method can further include removing the end effector from the sterile connector while maintaining the sterile barrier during a surgical procedure, coupling a second end effector to the sterile connector, and locking the second end effector to the sterile connector. Electrical signals can be passed through the sterile drape to notify a user when the sterile barrier is broken. In some such embodiments, the electrical signals can be passed through a conductive coating or conductive thread of the sterile drape.

Any of the features or variations described above can be applied to any particular aspect or embodiment of the present disclosure in a number of different combinations. The absence of explicit recitation of any particular combination is due solely to the avoidance of repetition in this summary.

DETAILED DESCRIPTION

Figure 1:
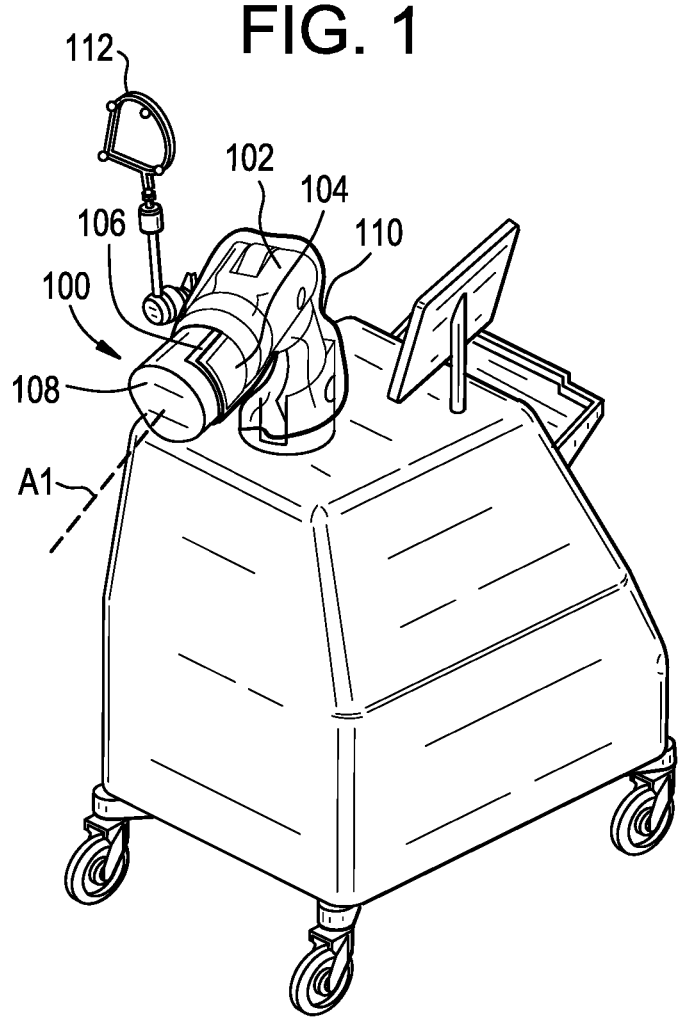
FIG. 1 is an illustration of an embodiment of a surgical robotic system of the present disclosure.
Figure 1A:
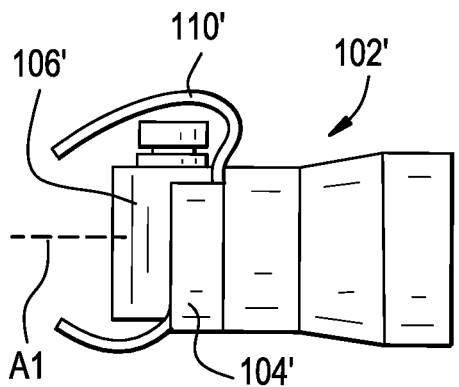
Figure 1B:
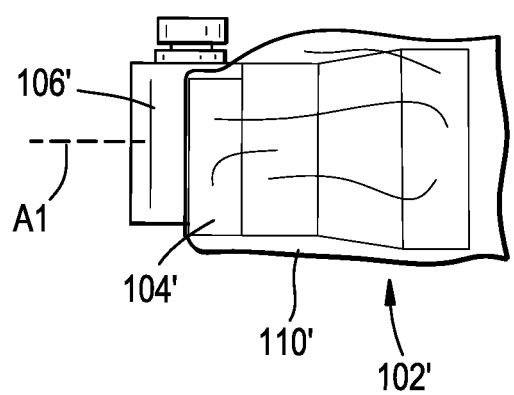

Robotic surgical systems and related methods are disclosed herein, e.g., for establishing and maintaining a sterile surgical field over the course of a surgical procedure such that an end effector can be swapped during the procedure without needing to re-sterilize or re-calibrate the surgical field. Robotic surgical assemblies of the present disclosure can include a robot arm, a sterile connector, and an end effector. The sterile connector can be coupled to a distal end of the robot arm such that the sterile connector can extend from a distal-most joint or portion of the robot arm (also referred to herein as a robot plate). A sterile drape can extend from a body of the sterile connector such that the sterile drape can extend or be draped over at least a portion of the robot arm. In this manner, the sterile connector, by virtue of the sterile drape, can establish a sterile barrier around the non-sterile robot arm. The portion of the robot arm under the sterile drape can then enter the surgical field without jeopardizing sterility. An end effector can couple to the sterile connector in a manner that can facilitate a hot swap or a change of end effectors during the surgical procedure without breaking the sterile barrier. The sterile connector and the end effector can be designed such that the sterile connector cannot be removed while an end effector is coupled thereto. Additionally, in some embodiments, the end effector can be prevented from coupling to the sterile connector until the sterile connector is locked to the robot arm. Such features can increase patient safety and can reduce the risk of destroying the sterile surgical field. In some embodiments, the sterile connector can include one or more signal connectors that can transmit at least one of light and electrical signals between the sterile connector and the robot arm and/or end effector. Accordingly, sterile connectors of the present disclosure can provide for added or enhanced functionality and control during a surgical procedure.

Certain exemplary embodiments will now be described to provide an overall understanding of the principles of the structure, function, manufacture, and use of the devices, systems, and methods disclosed herein. One or more examples of these embodiments are illustrated in the accompanying drawings. The devices, systems, and methods specifically described herein and illustrated in the accompanying drawings are non-limiting embodiments. The features illustrated or described in connection with one embodiment may be combined with the features of other embodiments. Such modifications and variations are intended to be included within the scope of the present disclosure.

Additionally, to the extent that linear or circular dimensions are used in the description of the disclosed devices and methods, such dimensions are not intended to limit the types of shapes that can be used in conjunction with such devices and methods. Equivalents to such linear and circular dimensions can be determined for different geometric shapes. Further, in the present disclosure, like-numbered components of the embodiments generally have similar features. Still further, sizes and shapes of the devices, and the components thereof, can depend at least on the anatomy of the subject in which the devices will be used, the size and shape of objects with which the devices will be used, and the methods and procedures in which the devices will be used.

FIG. 1 illustrates one embodiment of a surgical robotic system 100 of the present disclosure that can be attached to a robot arm 102. The robotic system 100 can include a robot plate 104, a sterile connector 106, and an end effector 108. The robot arm 102 can be a non-sterile component. The robot plate 104 can be a distal-most joint of the robot arm 102 and can be sterilized prior to a surgical procedure, e.g., can be wiped down to sterilize. In some embodiments the robot plate 104 can be integrally formed with the robot arm 102, while in other embodiments the robot plate 104 can be securely attached to the robot arm. The sterile connector 106 and the end effector 108 can be sterilized prior to the surgical procedure, e.g., each can be wiped to sterilize or can be removed from a sterile packaging within the sterile surgical field. While the end effector 108 shown is generic, i.e., does not include an instrument mount or a surgical instrument, any of a variety of end effector instrument mounts and/or instruments can be used within the scope of the present disclosure. In some embodiments, a navigation array 112 can be coupled to any of the robot arm 102, the sterile connector 106, or the end effector 108 to aid in positioning of the arm and/or any instrument coupled thereto.

A sterile drape 110 can extend from the sterile connector 106 and can drape over the robot plate 104 and at least a portion of the robot arm 102. The sterile drape 110 can be secured over the robot arm 102 such that a sterile barrier can be formed around the robot arm. For example, insert box A in FIG. 1 illustrates a sterile connector 106' coupled to a robot plate 104' of a robot arm 102'. The sterile connector 106' can be coupled to the robot plate 104' with a sterile drape 110' extending from a body of the sterile connector 106' in a rolled-up or everted configuration. In other words, the sterile connector 106' can be coupled to the robot plate 104' with the sterile drape 110' positioned such that at least a portion of the robot plate and the robot arm 102' are exposed. Once the sterile connector 106' is coupled to the robot plate 104', the sterile drape 110' can be unrolled or extended to cover the robot plate 104' and at least a portion of the robot arm 102' that may enter the surgical field during a surgical procedure, as can be seen in insert box B in FIG. 1. This can effectively create a sterile barrier around the robot plate 104' and the robot arm 102' that are covered by the sterile drape 110'.

The surgical robot system 100 can extend distally from the robot arm 102 along a central longitudinal axis A1 of the robot arm. As used herein, "proximal" can refer to a direction moving or facing towards the robot arm 102 along the central longitudinal axis A1, and "distal" can refer to a direction moving or facing away from the robot arm along the central longitudinal axis. "Interior," "inner," or "inwards" can refer to a direction moving or facing towards the central longitudinal axis A1, and "exterior," "outer," or "outwards" can refer to a direction moving or facing away from the central longitudinal axis A1. The term "radial" can refer to a direction that can intersect with the central longitudinal axis A1 at a transverse angle, i.e., a non-parallel relationship, which can include a 90-degree angle. The term "axial" can refer to a direction that can extend parallel to the central longitudinal axis A1.

Figure 2:
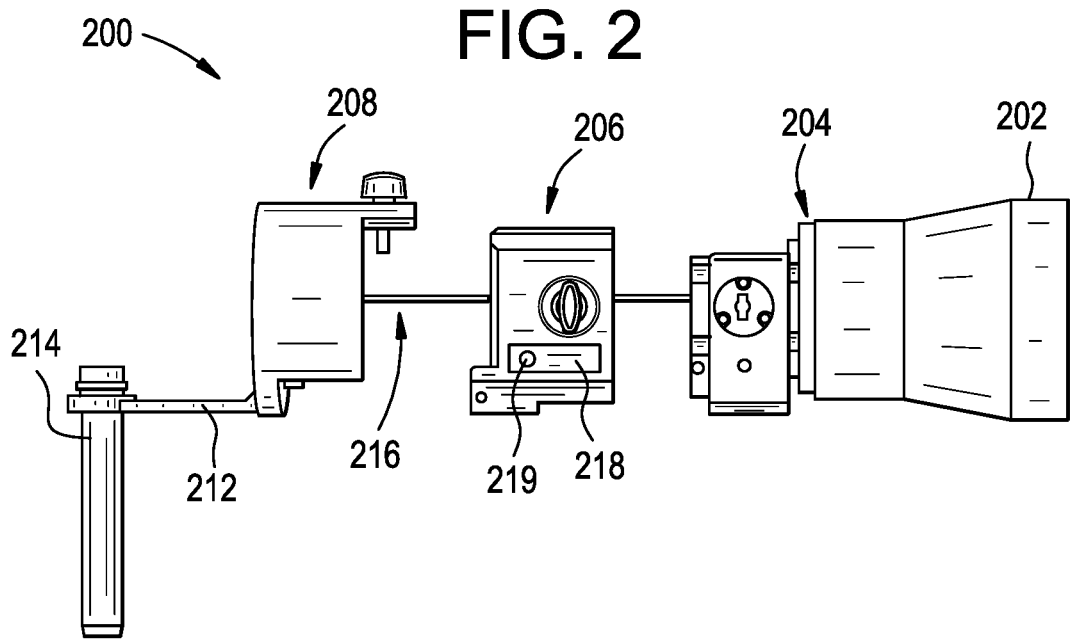
FIG. 2 is an exploded view of another embodiment of a surgical robotic system of the present disclosure showing a robot plate, a sterile connector, and an end effector.

FIG. 2 shows an exploded view of another embodiment of a surgical robotic system 200 of the present disclosure. The robotic system 200 can include a robot arm 202, a robot plate 204, a sterile connector 206, and an end effector 208. A sterile drape (not shown) can extend from the sterile connector 206 and can drape the robot arm 202 (see FIG. 1). The end effector 208 shown in FIG. 2 can include an instrument mount 212 that can receive an instrument e.g., an access port

214 at a distal end thereof. The robotic system 200 can maintain a sterile surgical field throughout the course of a surgical procedure that can include one or more "hot swaps" of instrumentation, i.e., replacing the end effector 208 that is attached to the sterile connector 206 to allow use of different surgical instruments coupled to or received by the various end effectors. Put another way, the end effector 208 and/or the instrument 214 can be swapped during the surgical procedure without breaking a sterile barrier.

Figure 3:
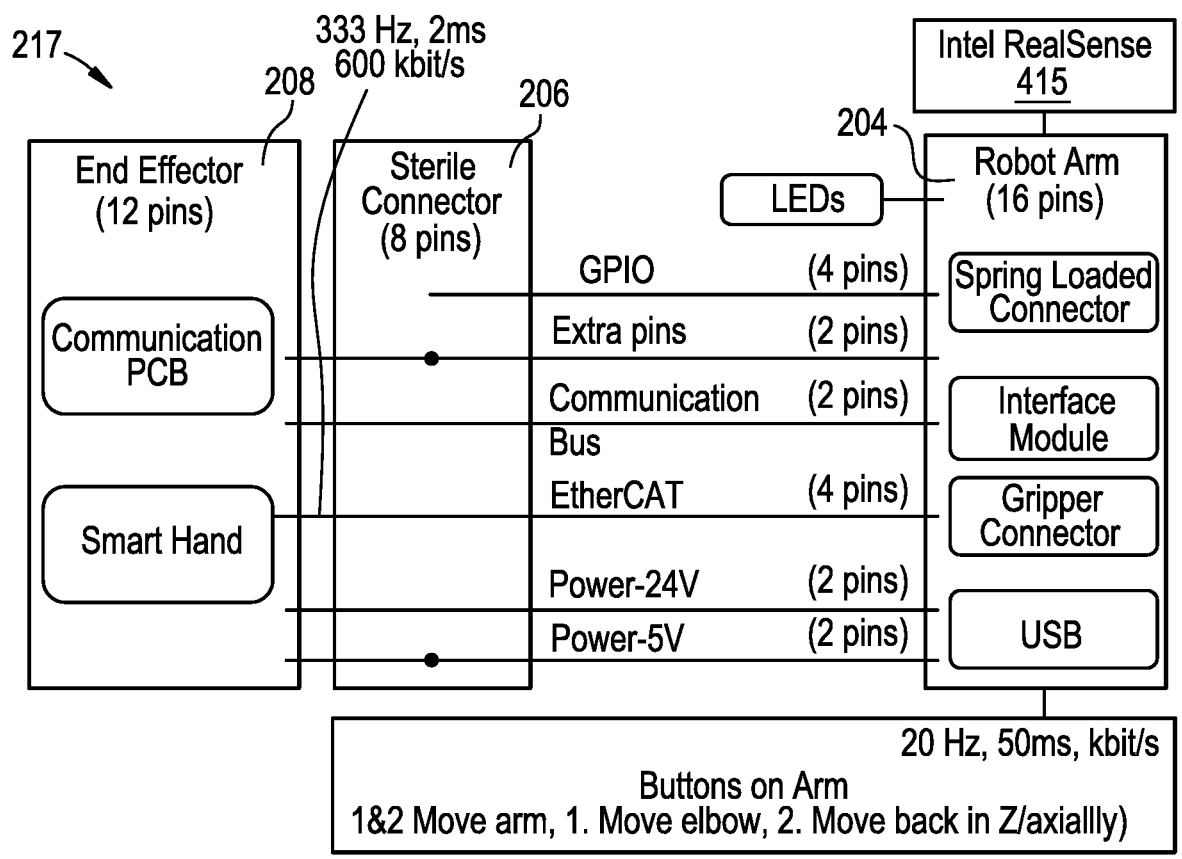
FIG. 3 is a schematic diagram of one embodiment of a communication scheme that can be utilized in accordance with the present disclosure.

As discussed in detail below, the sterile connector 206 can include one or more signal connectors that can couple with one or more counterpart signal connectors in the robot plate 204 and/or end effector 208, which can facilitate transmission of signals therebetween. In some embodiments, the sterile connector 206 can facilitate transmission of electrical signals, such as power signals, data, instructions, commands, etc., between and among the robot arm 202 (via the robot plate 204), the sterile connector 206, and the end effector 208. For example, a communication bus 216 can pass electrical signals from the robot plate 204 through the sterile connector 206 to the end effector 208 and vice-versa. In some instances, electrical signals can be intended to pass between the sterile connector 206 and only one of the robot plate 204 and the end effector 208. FIG. 3 shows one embodiment of an electrical communication scheme 217, which can be implemented by the communication bus 216 to transmit signals between the robot arm 202, the sterile connector 206, and the end effector 208. In some embodiments, the sterile connector 206 can include a printed circuit board (PCB) that can facilitate user interaction and/or the communication of electrical signals. The sterile connector 206 can transmit data between the end effector 208 and the robot arm 202 such that software and computer systems used in conjunction with the robotic procedure can interpret and present information to a user.

Returning to FIG. 2, in some embodiments, the sterile connector can provide for direct user interaction through a user interface 218. The user interface 218 can be located on an outer surface of the sterile connector 206 such that at least a portion of the interface can be accessed by a user during the surgical procedure. In some embodiments, a user can control one or more features of the robot arm 204 and/or the end effector 208 through the user interface 218. The user interface 218 can include one or more buttons, knobs, indicators, etc., through which the user can input and/or receive information. For example, the user interface 218 can include one or more buttons or other input mechanisms (e.g., knobs, potentiometers, joysticks, etc.) that can change robot arm 202 parameters (e.g., sensitivity to outside forces, robot arm speed, robot sensitivity) and/or a position of the robot arm. In some embodiments, a user can change a robot arm control mode, e.g., can toggle between a locked and an unlocked state of the arm, can constrain movement of the robot arm along a trajectory, etc. Additionally, or alternatively, a user can interact with the end effector 208 through the user interface 218. By way of non-limiting example, a user can adjust parameters, such as to fine-tune a depth, speed, and/or frequency of an end effector or instrument coupled thereto, and can override allowable boundaries of an instrument. The user interface 218 can also provide information to the user. For example, the user interface 218 can include one or more visual indicators, such as a light emitting diode (LED) 219, that can notify a user of certain information or conditions, e.g., when the sterile connector 206 and/or the end effector 208 are in a locked position; when the end effector is coupled to the sterile connector; if the end effector is approaching an allowable boundary for the particular end effector; if a navigation system is no longer tracking the robot due to, for example, a visual obstruction, etc.

Figure 4:
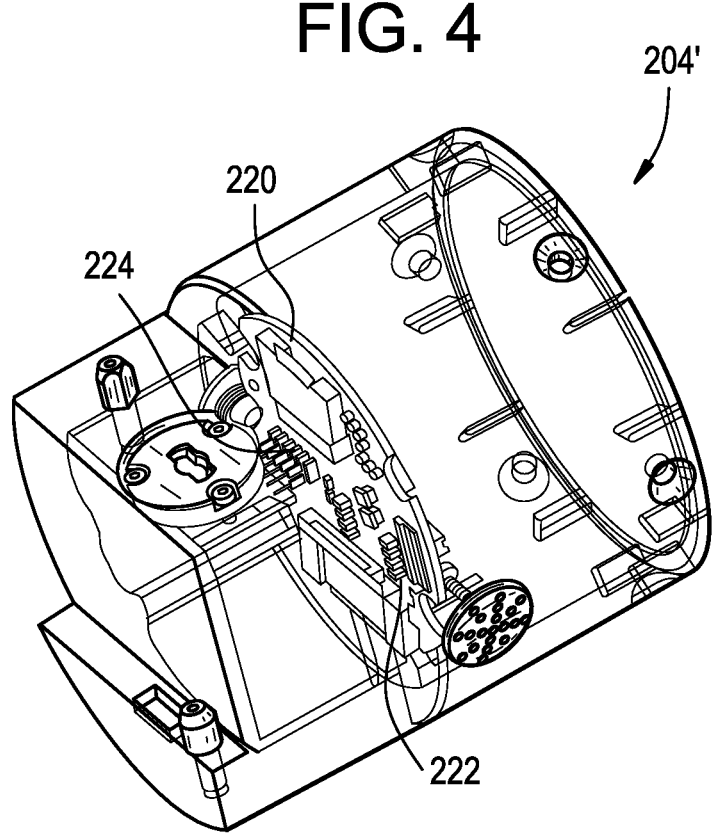
FIG. 4 is an illustration of another embodiment of a robot plate of the present disclosure.

FIG. 4 shows another embodiment of a robot plate 204' that can include an integrated printed circuit board (PCB) 220. The robot plate 204' can be coupled with the sterile connector 206 such that the PCB 220 can couple with a signal connector of the sterile connector and can communicate electrical signals between the robot plate 204' and the sterile connector 206. For example, the PCB can include a first set of electrical contacts 222 and a second set of electrical contacts 224, each of which can engage with complementary contacts of one or more signal connectors in a sterile connector body (see FIGS. 11-21). A PCB, such as the PCB 220, can, additionally or alternatively, be integrated within a body of the sterile connector 206 and/or the end effector 208, which can provide for additional communication functionality between the components.

Figure 5:
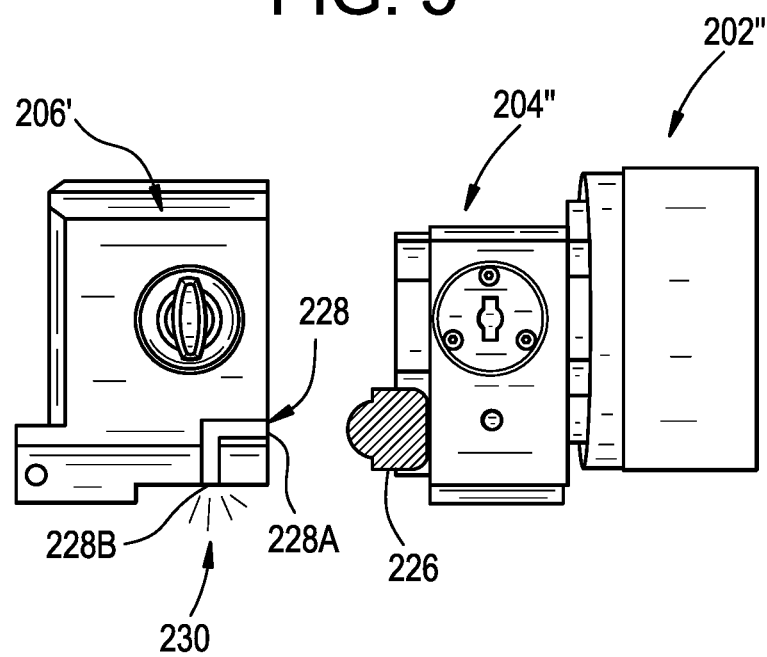
FIG. 5 is an illustration of another embodiment of a sterile connector and a robot plate of the present disclosure.

In some embodiments, a sterile connector of the present disclosure can include one or more signal connectors that can pass light through at least a portion of the sterile connector. FIG. 5 illustrates another embodiment of a sterile connector 206' that can transmit light from a robot plate 204". A light source, such as a light emitting diode (LED) 226, can be built into or otherwise attached to the robot plate 204". For example, the LED 226 can extend from a distal facing surface of the robot plate 204". The sterile connector 206' can include a signal connector 228, such as a light pipe or passage, that can direct light through at least a portion of the sterile connector such that the light axially or radially exits the sterile connector. The light passage 228 can extend from an entrance 228A through the sterile connector 206" to an exit 228B. The sterile connector 206" can be coupled to the robot plate 204" such that the entrance 228A of the light passage 228 can align with the LED 226. Light from the LED 226 can thus enter the light passage 228 at the entrance 228A and can be directed by the light passage 228 to the exit 228B such that light 230 can shine from an outer surface of the sterile connector.

While the illustrated embodiment of FIG. 5 shows the sterile connector 206' with one light passage 228 that can direct light that enters the sterile connector axially to an exit located on a radial outer surface of the sterile connector, other arrangements are within the scope of the present disclosure. For example, in some embodiments, the light passage 228 can extend axially through the sterile connector 206' such that light can exit the sterile connector through an exit 228B on a distal facing surface of the sterile connector. Furthermore, in some embodiments, the exit 228B of the light passage 228 can align with an entrance of a light passage in an end effector (not shown). In this manner, light from the LED 226 of the robot plate 204" can be transmitted through the sterile connector 206' to the end effector 208. In other embodiments, the light passage 228 of the sterile connector 206' can have an entrance 228A that can align with an LED or other light source that can extend from the end effector 208.

Figure 6:
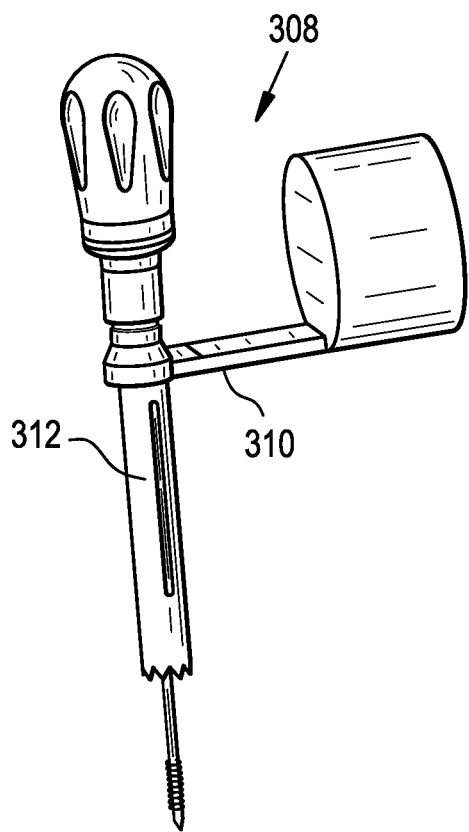
FIGS. 6-8 each illustrate embodiments of end effectors that can be used in the surgical robotic system of the present disclosure.
Figure 7:
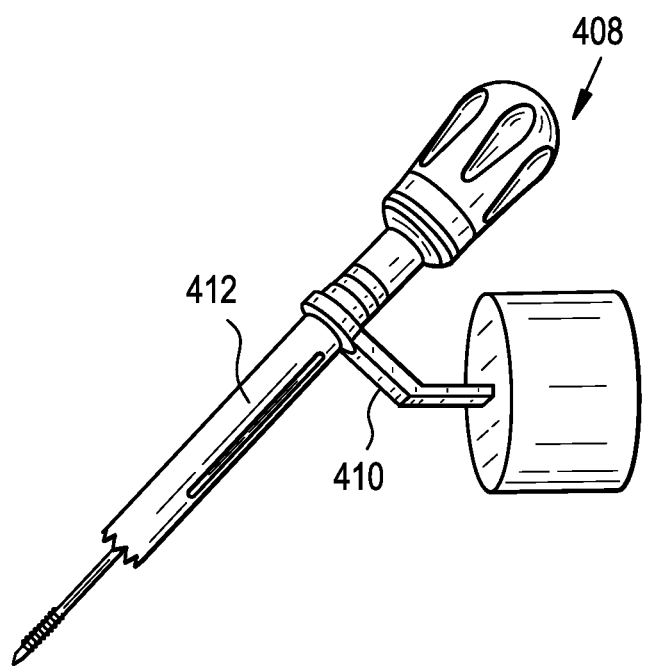
Figure 8:
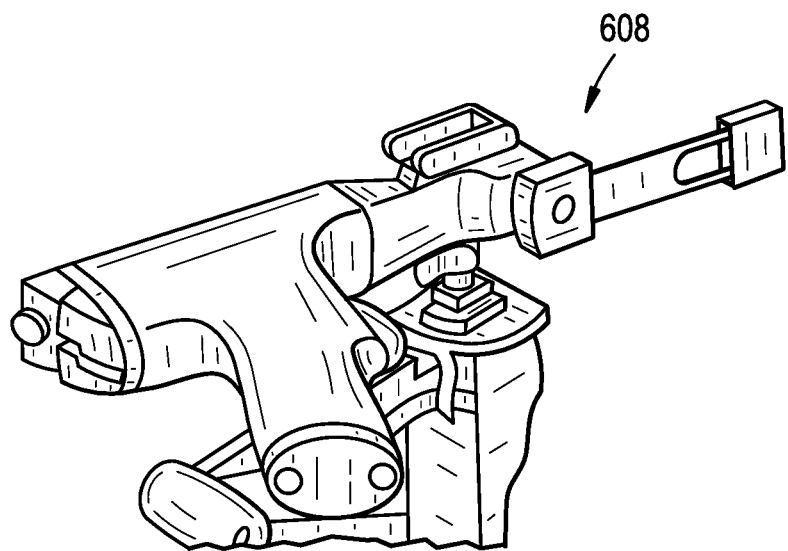

FIGS. 6-8 show non-limiting embodiments of end effectors and surgical tools that can be used in the surgical robotic systems disclosed herein. FIG. 6 shows a drill-tap-screw (DTS) guide end effector 308. An instrument mount 310 can hold an instrument 312, e.g., a drill, tap, saw, or combination instrument, with a perpendicular trajectory relative to a longitudinal axis of the end effector. FIG. 7 shows another embodiment of a DTS guide end effector 408 that includes an instrument mount 410 that can hold an instrument 412 at an angled or oblique trajectory relative to a longitudinal axis of the end effector. FIG. 8 illustrates an oscillating saw end effector 608 that can be used, for example, in a surgical procedure on a shoulder or knee. The end effectors 508, 608 can be part of a surgical robotic system of the present disclosure that can include transmission of electrical signals such that power and control signals can be provided to the end effectors and surgical instruments through a sterile connector of the present disclosure.

FIGS. 9-21 illustrate another embodiment of a robotic surgical system 1000 of the present disclosure. The robotic surgical system 1000 can include a robot plate 1004 at a distal end of a robot arm 102 (see FIG. 1), a sterile connector 1006, and an end effector 1008. The sterile connector 1006 can include a sterile drape 1010. In some embodiments, the sterile drape 1010 can be sandwiched between a first portion 1006A of the sterile connector and a second portion 1006B of the sterile connector. The sterile connector 1006 can be coupled to the robot plate 1004 such that the sterile drape 1010 can extend over the robot plate 1004 and at least a portion of the robot arm 102, and can create a sterile barrier around the robot plate and the robot arm. In some embodiments, the sterile drape 1010 can include a conductive coating and/or one or more conductive threads, which can transmit electrical signals through the sterile drape. For example, a user can be alerted if the sterile barrier has been broken or if a connection between the sterile connector and the robot plate and/or the end effector becomes disconnected by monitoring electrical signals passed through the sterile drape. For example, signals passed through the sterile drape can be monitored and utilized to trigger illumination of an LED or other visual alert located on a component of the robotic surgical system 1000, to trigger an alarm sound, or to log information in a connected server or computing system.

Figure 10:
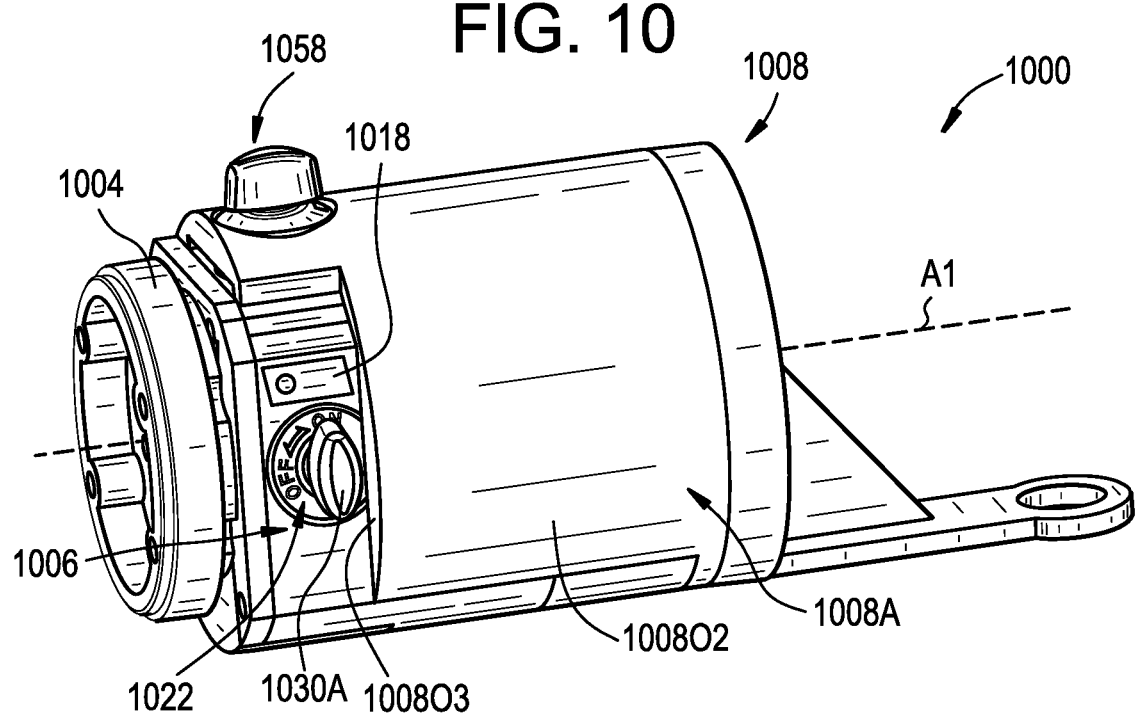
FIG. 10 is another perspective view of the surgical robotic system of FIG. 9.
Figure 11:
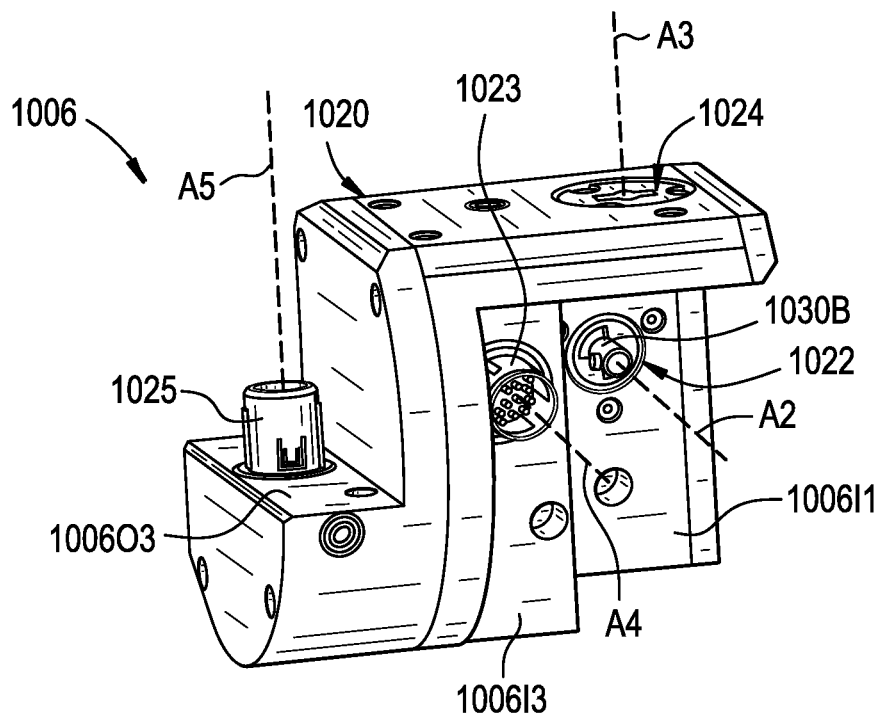
FIG. 11. is a perspective of the sterile connector of FIG. 9.

Electrical signals can be communicated through the system 1000 through one or more signal connectors that can be included in the robot plate 1004, the sterile connector 1006, and the end effector 1008. In some embodiments, the sterile connector 1006 can have a user interface 1018 located on an outer surface thereof. The user interface 1018 can include any of the features described with reference to the user interface 218 above. The user interface 1018 can be placed anywhere on an outer surface of the sterile connector 1006 such that at least a portion of the interface can be accessed by a user when the sterile connector 1006 is coupled to the robot plate 1004. Moreover, in some embodiments, and as illustrated in FIG. 10, at least a portion of the user interface 1018 can be accessible to a user when the end effector 1008 is coupled to the sterile connector 1006.

The sterile connector 1006 will now be described in greater detail with reference to FIGS. 11-14. The sterile connector 1006 can include a body 1020, a first component connector 1022 that can couple the sterile connector to the robot plate 1004, and a second component connector 1024 that can couple the sterile connector to the end effector 1008. The sterile connector 1006 can also include a first signal connector 1023 that can transmit signals between the sterile connector and the robot plate 1004, and a second signal connector 1025 that can transmit signals between the sterile connector and the end effector 1008. A central longitudinal axis A1' of the sterile connector 1006 can extend parallel to the central longitudinal axis A1 of the assembled system 1000. One or more of the first component connector 1022, the second component connector 1024, the first signal connector 1023, and the second signal connector 1025 can extend along an axis of the sterile connector 1006 transverse to the central longitudinal axis A1. For example, the first component connector 1022 can extend along an axis A2, the second component connector 1024 can extend along an axis A3, the first signal connector can extend along an axis A4, and the second signal connector can extend along an axis A5. In some embodiments, each of the axes A2, A3, A4, and A5 can extend transverse relative to the central longitudinal axis A1 of the sterile connector. Moreover, one or more of the axes A2, A3, A4, and A5, can extend transverse relative to one another. For example, the first component connector 1022 can extend transverse to the second component connector 1024 (i.e., the axis A2 of the first component connector 1022 can extend in a non-parallel relationship to the axis A3 of the second component connector 1024).

Turning now to the component connectors 1022, 1024, the first component connector 1022 can extend radially through the body 1020 of the sterile connector 1006 towards the central longitudinal axis A1 of the sterile connector. More particularly, the first component connector 1022 can extend from an outer surface 1006O1 of the body 1020 to an inner surface 1006I1 of the body along the axis A2. The first component connector 1022 can facilitate radially coupling the sterile connector 1006 to the robot plate 1004 along the axis A2. In some embodiments, the first component connector 1022 can include a lock 1030 that can be movable between a first position in which relative movement between the sterile connector 1006 and the robot plate 1004 can be restricted (i.e., a locked position) and a second position in which the sterile connector can be separated from the robot plate (i.e., an unlocked position).

Figure 12:
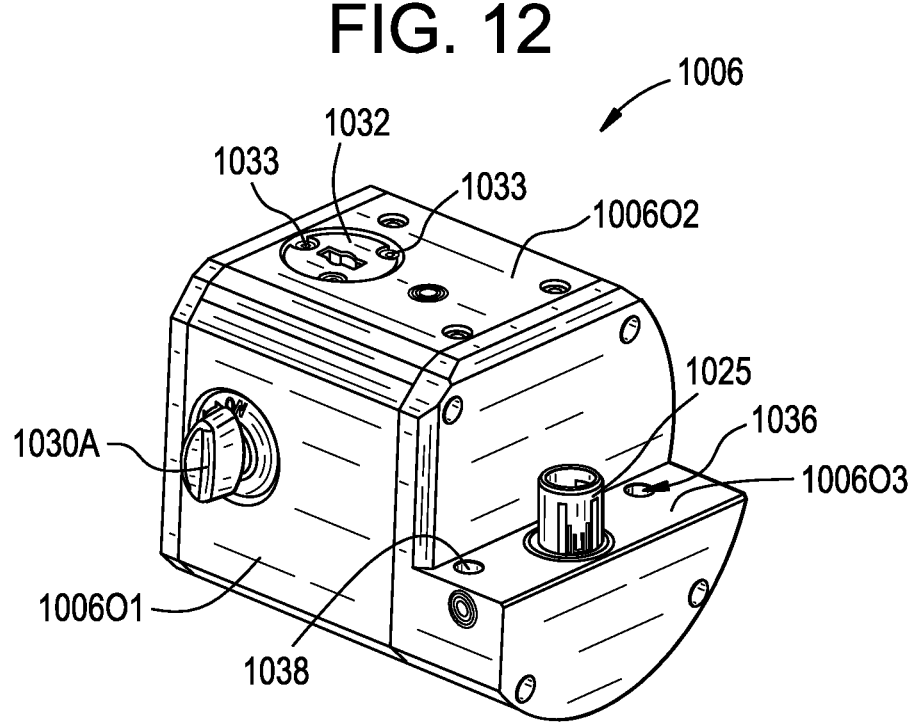
FIG. 12 is another perspective view of the sterile connector of FIG. 9.
Figure 13:
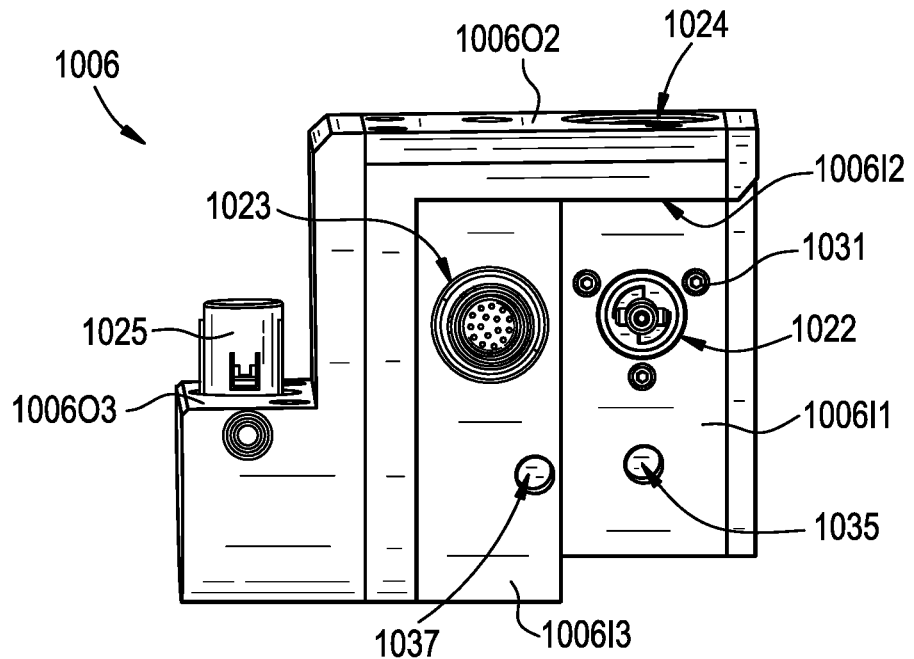
FIG. 13 is a lateral view of the sterile connector of FIG. 9.
Figure 14:
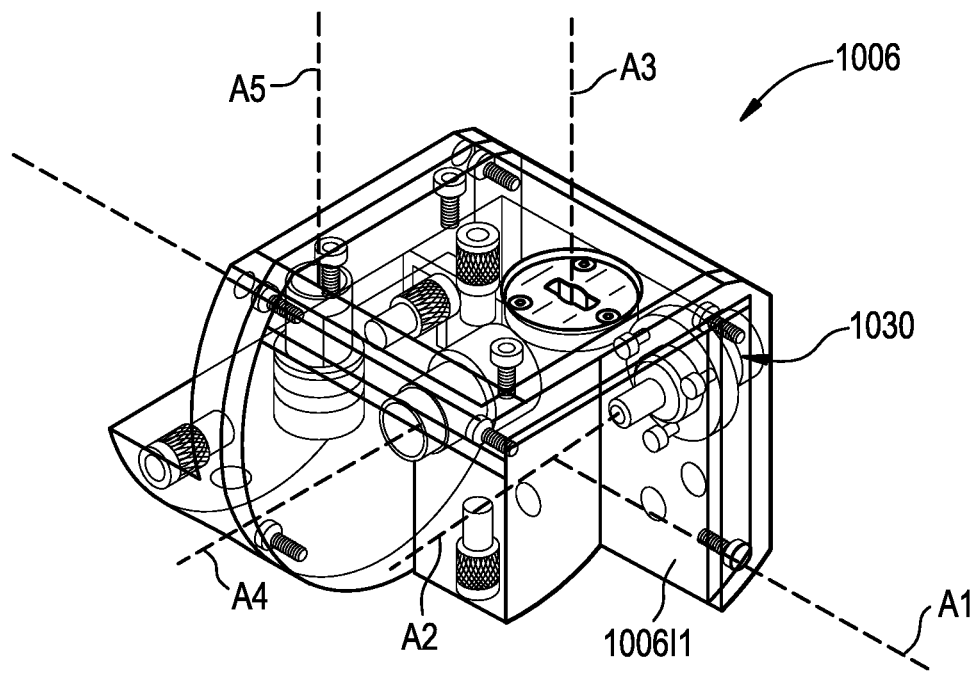
FIG. 14 is a partially-transparent perspective view of the sterile connector of FIG. 9.

By way of non-limiting example, the lock 1030 can be a quarter-turn lock with a handle 1030A and a locking shaft 1030B. The locking shaft 1030B can couple with a corresponding component connector 1040 of the robot plate 1004. The lock handle 1030A can extend from the outer surface 1006O1 of the body and can be accessed by a user, even when the system 1000 is in the assembled configuration (see FIGS. 9 and 10). The locking shaft 1030B can extend through the body 1020 and can protrude from the inner surface 1006I1 towards the central longitudinal axis A1 of the sterile connector 1006. In some embodiments, as can be seen in FIG. 12, the lock 1030 can be in the locked first position with the lock handle 1030A perpendicular or substantially perpendicular to the central longitudinal axis A1. The lock handle 1030A can be rotated or turned to a position parallel or substantially parallel to the central longitudinal axis A1, which can place the lock 1030 in the second unlocked position. In some embodiments, the lock handle 1030A can be rotated or turned about 90 degrees to move the lock between the first position and the second position. In some embodiments, the first component 1022 can include visual indicators, such as, for example, text reading "ON" and "OFF" that can correspond to the orientation of the lock handle 1030A in the first and second position, respectively.

The second component connector 1024 can extend radially through the body 1020 of the sterile connector 1006 along the axis A3 towards the central longitudinal axis A1. More particularly, the second component connector 1024 can extend from an outer surface 1006O2 of the body 1020 to an inner surface 1006I2 along the axis A3. In some embodiments, the axis A3 of the second component connector and the axis A2 of the first component connector 1022 can extend transverse, and in some embodiments orthogonal, to one another. Moreover, in some embodiments, one or both of the first component connector axis A2 and the second component connector axis A3 can extend orthogonal to the central longitudinal axis A1 of the sterile connector 1006. As will be discussed in detail below, the second component connector 1024 can facilitate radially coupling the sterile connector 1006 to the end effector 1008. In some embodiments, the second component connector 1024 can include a lock receptacle 1032. The lock receptacle 1032 can receive a complementary component connector 1058 of the end effector 1008 such that the complementary component connector of the end effector can be moved between a first position in which relative movement between the end effector and the sterile connector can be restricted and a second position in which the end effector can be separated from the sterile connector.

The sterile connector 1006 can include one or more signal connectors that can transmit signals, such as power signals, electrical communication signals, light, etc., between the sterile connector and at least one of the robot plate 1004 and the end effector 1008. In the illustrated embodiment, the first signal connector 1023 can transmit signals between the sterile connector 1006 and the robot plate, and the second signal connector 1025 can transmit signals between the sterile connector and the end effector 1008. The first signal connector 1023 can extend radially from an inner surface 1006I3 of the body 1020 along an axis A4 towards the central longitudinal axis A1. The axis A4 can be transverse to the central longitudinal axis A1 such that the first signal connector 1023 can extend radially inward from the body 1020. The first signal connector 1023 can couple with a complementary signal connector 1050 of the robot plate 1004, which can create an electrical path between the sterile connector and the robot plate. The first signal connector 1023 can send and receive electrical signals between the sterile connector and the robot plate. In some embodiments, the first signal connector 1023 can extend parallel to the first component connector 1022 such that a physical coupling of the sterile connector 1006 and the robot plate 1004 and a signal transmission coupling between the sterile connector and the robot plate can occur along parallel but distinct axes, e.g., axis A2 and axis A4, respectively.

The second signal connector 1025 can extend from an outer surface 1006O3 of the body 1020 along an axis A5. The axis A5 of the second signal connector 1025 can be transverse to the central longitudinal axis A1. In some embodiments, the axis A5 can extend orthogonally relative to the central longitudinal axis A1. The second signal connector 1025 can couple with a complementary signal connector 1064 of the end effector 1008, which can create an electrical path between the sterile connector 1006 and the end effector. The second signal connector 1025 can send and receive electrical signals between the sterile connector 1006 and the end effector 1008. In some embodiments, the second signal connector 1025 can extend parallel to the second component connector 1022 such that a physical coupling of the sterile connector 1006 and the end effector 1008 and a signal transmission coupling between the sterile connector and the end effector can occur along parallel, but distinct, axes, e.g., axis A3 and A5, respectively.

The body 1020 of the sterile connector 1006 can include one or more additional mating features that can mate with counterpart mating features of the robot plate 1004 and the end effector 1008. These additional mating features can aid with alignment of the components and can increase stability of a coupling between the sterile connector and the robot plate and end effector. For example, the body 1020 can include one or more pin recess 1035, 1037, 1036, 1038, which can act as female mating features that can align with and receive counterpart male mating features of the robot plate and the end effector (described in detail below).

Alternative arrangements of the mating features are within the scope of the present disclosure. For example, the sterile connector 1006 can have male mating features with counterpart female mating features on the robot plate and end effector. Moreover, placement and number of such features can be varied.

Figure 15:
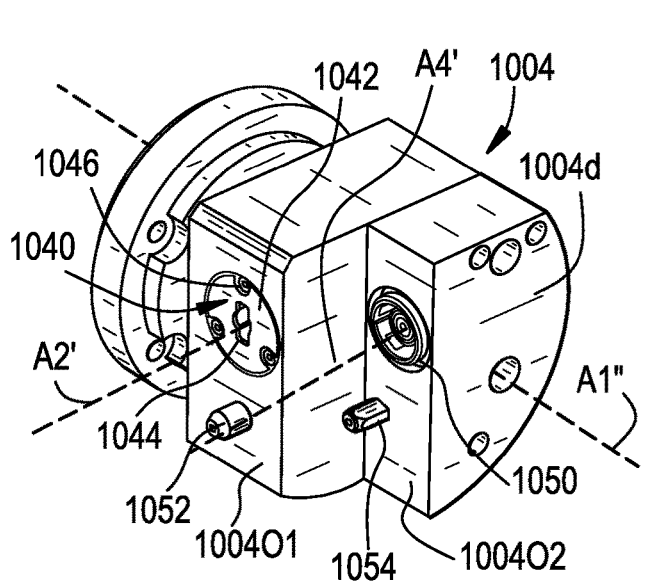
FIG. 15 is a perspective view of the robot plate of FIG. 9.
Figure 16:
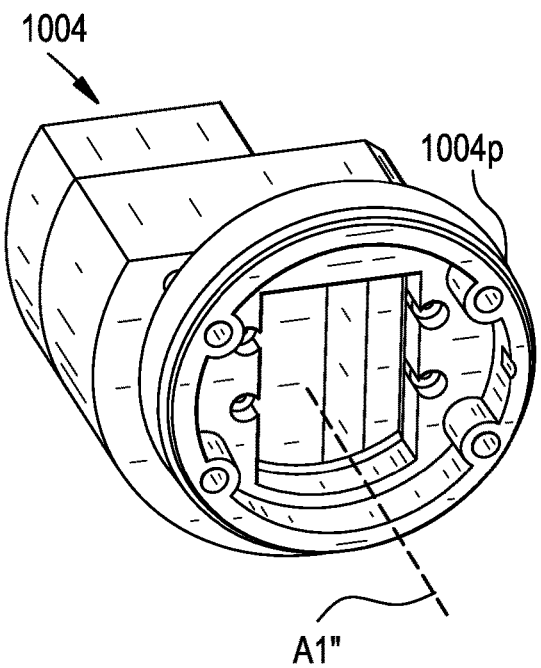
FIG. 16 is another perspective view of the robot plate of FIG. 9.

FIGS. 15 and 16 show perspective views of the robot plate 1004. The robot plate 1004 can be generally cylindrical and can extend along a central longitudinal axis A1 from a proximal end 1004p to a distal end 1004d. The proximal end 1004p of the robot plate 1004 can be integrally formed with the robot arm 102 (see FIG. 1) or can be otherwise securely attached to a distal end of the robot arm such that the robot plate 1004 can form or be a part of a distal-most joint of the robot arm. A geometry of the robot plate 1004 can be complementary to an inner surface geometry of the sterile connector 1006 such that the robot plate and the sterile connector can be brought into alignment along a radial axis, i.e., an axis extending transverse relative to the central longitudinal axis A1 of the robotic surgical system 1000.

The robot plate 1004 can include a component connector 1040 that can couple with the first component connector 1022 of the sterile connector 1006. The component connector 1040 can extend through an outer surface 1004O1 of the robot plate 1004 along an axis A2'. The axis A2' of the component connector 1040 can extend transverse relative to the central longitudinal axis A1", and, in some embodiments, can extend orthogonally relative to the central longitudinal axis. The robot plate outer surface 1004O1 with the component connector 1040 can have a complementary geometry to the sterile connector inner surface 1006I1 with the first component connector 1022. In some embodiments, the robot plate component connector 1040 can include a lock receptacle 1042 that can be complementary to the lock 1030 of the sterile connector's first component connector 1022 A slot 1044 of the lock receptacle 1042 can receive the locking shaft 1030B of the lock 1030 such that the lock 1030 can be moved between a locked position and an unlocked position. The lock receptacle 1042 can also include one or more recesses 1046 that can receive counterpart protrusions 1031 of the lock 1030.

The robot plate 1004 can also include a signal connector 1050 that can couple with the sterile connector's first signal connector 1023. The signal connector 1050 can extend from an outer surface 1004O2 into the robot plate along an axis A4'. The axis A4' of the signal connector can extend transverse to the central longitudinal axis A1. Pins 1052, 1054 can extend radial from outer surfaces 1004O1, 1004O2, respectively, of the robot plate 1004. As discussed above, the pins 1025, 1054 can act as male mating features and can be received within counterpart female mating features of the sterile connector 1006, e.g., pin recesses 1035, 1037, respectively.

Figure 17:
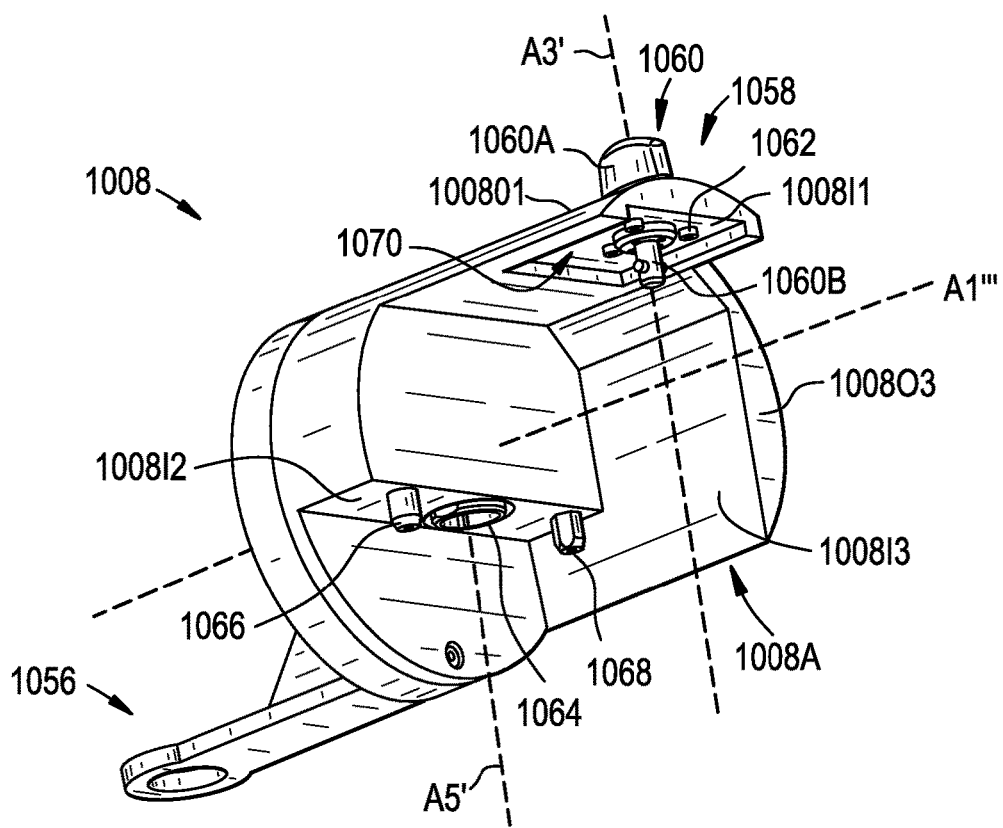
FIG. 17 is a perspective view of the end effector of FIG. 9.

FIG. 17 shows a perspective view of the end effector 1008. The end effector 1008 can couple to the sterile connector 1006 such that the end effector can be securely attached to the robot arm 102 for use during a surgical procedure. The end effector 1008 can include a surgical instrument or instrument guide (e.g., access port 214 shown in FIG. 2) that can either be integrally formed with the end effector 1008 or can be removably received within an instrument mount 1056. In some embodiments, the end effector 1008 can be generally cylindrical and can extend along a central longitudinal axis A1'''. The end effector 1008 can include a component connector 1058 that can couple with the sterile connector's second component connector 1024. The end effector component connector 1058 can extend through the end effector from an outer surface 1008O1 to an inner surface 1008I1 along an axis A3'. The axis A3' of the component connector 1058 can extend transverse relative to the central longitudinal axis A1'''.

In some embodiments, the component connector 1058 can include a lock 1060 that can be received within the sterile connector's second component connector 1024 and, more particularly, within the lock receptacle 1032 of the second component connector 1024. The lock 1060 can be movable within the lock receptacle 1032 between a first position (i.e., a locked position) in which relative movement between the end effector 1008 and the sterile connector 1006 can be restricted and a second position (i.e., an unlocked position) in which the end effector can be separated from the sterile connector. In some embodiments, the lock 1060 can be a quarter-turn lock, similar to that described above, having a lock handle 1060A and a locking shaft 1060B. The lock handle 1060A can extend from the outer surface 1008O1 of the end effector and can be access by a user. The locking shaft 1060B can extend beyond the inner surface 1008I1 towards the central longitudinal axis A1'''. The locking shaft 1060B can be received within the lock receptacle 1032 of the sterile connector, and the lock handle 1060A can be turned by the user to move the lock 1060 between the first position and the second position. The end effector component connector 1058 can also include one or more protrusions 1062 that can extend radially inwards from the inner surface 1008I1. The protrusions 1062 can be received within complementary recesses 1033 of the sterile connector lock receptacle 1032, which can aid in alignment and coupling of the end effector and the sterile connector.

The end effector 1008 can also include a signal connector 1064 that can couple with the sterile connector's second signal connector 1025. In some embodiments, the end effector signal connector 1064 can be a female electrical connector and the sterile connector's second signal connector 1025 can be a counterpart male electrical connector. The end effector signal connector 1064 and the sterile connector second signal connector 1025 can be coupled and can establish a signal transmission path between the end effector 1008 and the sterile connector 1006. The signal connector 1064 can extend from an inner surface 1008I2 into the end effector 1008 along an axis A5'. The axis A5' of the signal connector can extend transverse relative to the central longitudinal axis A1'''. Pins 1066, 1068 can extend radially, parallel to the axis A5', from the inner surface 1008I2. As discussed above, the pins 1066, 1068 can serve as male mating features and can be received within counterpart female mating features of the sterile connector 1006, e.g., pin recesses 1036, 1038, respectively.

An inner surface geometry of the end effector 1008, i.e., a geometry of end effector surfaces facing towards the longitudinal axis A1''', can complement at least a portion of an outer surface geometry of the sterile connector 1006 such that stability of the coupling between the sterile connector and the end effector can be increased. For example, in some embodiments, the inner surface 1008I1 of the end effector can include a notched or recessed portion 1070. The recessed portion 1070 can have a complementary negative geometry to a portion of the sterile connector outer surface 1006O2' such that the surfaces can align and fit together with a complementary relationship.

The end effector 1008 can have a sidewall extension 1008A with an inner surface 1008I3 and an outer surface 1008O2 (see FIG. 10). The inner surface 1008I3 of the extension 1008A can have a complementary geometry to an outer surface 1006O1 of the sterile connector 1006. The outer surface 1008O2 of the extension 1008A can be generally cylindrical such that, in the fully assembled configuration of the robotic surgical system 1000, the cylindrical outer surface of the extension can form a cylindrical exterior surface of the assembled robotic surgical system.

With particular reference to FIGS. 10 and 17, the extension 1008A can serve as a mechanical stop or block that can prevent removal of the sterile connector 1006 from the robot plate 1004 while the end effector 1008 is coupled to the sterile connector. The extension 1008A can be dimensioned such that, when the end effector 1008 is coupled to the sterile connector 1006, a proximal-facing outer surface 1008O3 of the extension 1008A can be located within a close proximity to the first component connector 1022 of the sterile connector. More particularly, the extension's proximal-facing outer surface 1008O3 can be placed such that the lock handle 1030A of the lock 1030 cannot be moved from the locked first position (i.e., the position shown in FIG. 10 with the handle 1030A in a substantially vertical orientation) to the unlocked second position. This is because the handle 1030A can be mechanically blocked from moving out of the substantially vertical orientation of the first position to the unlocked second position by the end effector extension 1008A. If a user attempted to turn the handle 1030A from the first position in either a clock-wise or counter-clockwise direction, the handle 1030A would physically interfere with the extension 1008A and can thus be prevented from moving to the unlocked second position. In other words, the end effector 1008 with the extension 1008A can ensure that the sterile connector 1006 can only be unlocked from the robot plate 1004 when there is no end effector attached. Accordingly, a user can be prevented from prematurely removing the sterile connector 1006 and the sterile drape 1010, which can aid in maintaining sterility of the surgical field over the course of a surgical procedure.

Moreover, the extension 1008A can mechanically prevent attachment of the end effector 1008 to the sterile connector 1006 before the sterile connector 1006 can be coupled and locked to the robot plate 1004. The extension 1008A can allow for proper engaging alignment of the end effector's component connector 1058 with the counterpart sterile connector's second component connector 1024 only when the sterile connector's first component connector lock handle 1030A is in the locked position, i.e., the position in which relative movement between the sterile connector and the robot plate 1004 can be locked. This is because in the lock handle's 1030A unlocked position, the lock handle can be in a horizontal or substantially horizontal position, which can cause the extension 1008A and, more specifically, the proximal facing outer surface 1008O3, to abut the lock handle 1030A. This interference can prevent alignment of the lock 1060 of the end effector's component connector 1058 with the lock receptacle 1032 of the sterile connector's second component connector 1024. In this manner, the construction and interaction of the end effector 1008 and the sterile connector 1006 can prevent coupling of the end effector with the sterile connector when the sterile connector is not properly locked to the robot plate 1004. Moreover, in some embodiments, a position of the lock 1060 can be detected by a sensor (not shown) that can monitor a degree of rotation of the lock and can determine if the lock is in the locked or unlocked position. Data regarding the position of the lock 1060 can be transmitted to a user, for example, by way of a transmission path established by coupling the sterile connector's first signal connector 1023 with the robot plate signal connector 1050. A position of the end effector lock 1060 may be similarly monitored.

Figure 18:
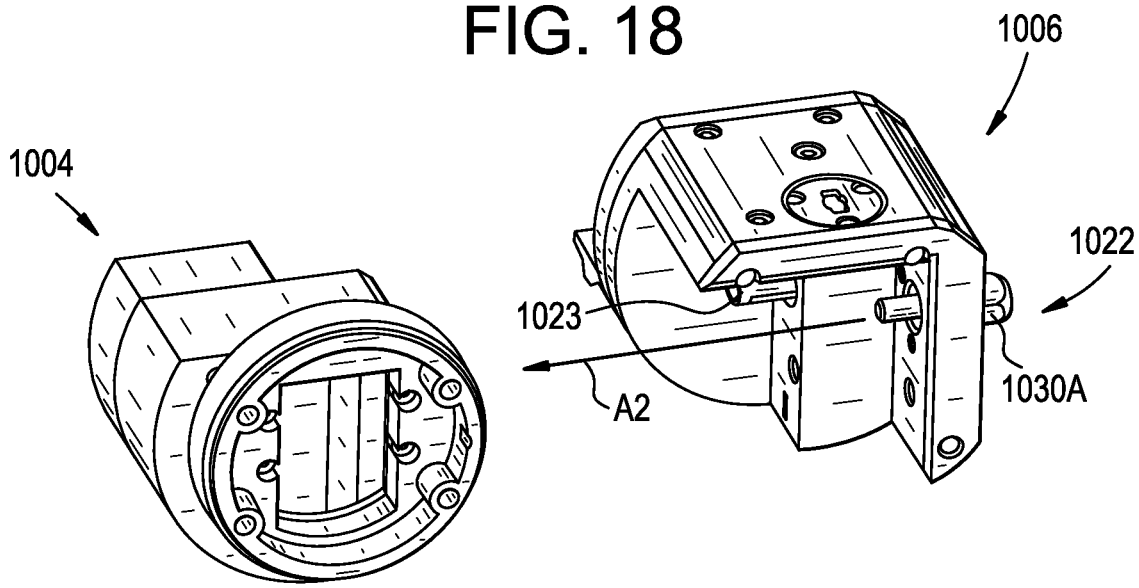
FIG. 18 illustrates a step in one embodiment of coupling the sterile connector of FIG. 9 to the robot plate of FIG. 9.

One embodiment of a method of assembling the robotic surgical system 1000 will now be described with reference to FIGS. 18 and 19. FIG. 18 illustrates an embodiment of radially coupling the sterile connector 1006 to the robot plate 1004. While not illustrated in FIG. 18, the robot plate 1004 can be securely attached to the robot arm 102 (see FIG. 1), and can thereby form or be a part of a distal-most joint or end of the robot arm. The sterile connector 1006 can be moved towards the robot plate 1004 radially, i.e., along the axis A2 that can extend transverse to the central longitudinal axis A1. The lock 1030 of the first component connector 1022 can be placed in the unlocked position, as shown in FIG. 18. The sterile connector 1006 can be moved relative to the robot plate 1004 such that the locking shaft 1030B of the lock 1030 can be inserted into the lock receptacle 1042 of the robot plate component connector 1040 along the transverse axis A2. The first signal connector 1023 of the sterile connector 1006 can be inserted into or otherwise couple with the signal connector 1050 of the robot plate 1004 along the transverse axis A4. Accordingly, the sterile connector 1006 can be radially coupled to the robot plate 1004 such that the sterile connector can extend distally from the robot plate along the central longitudinal axis A1.

In some embodiments, one or more surfaces of the sterile connector 1006 can abut one or more surfaces of the robot plate 1004 when the sterile connector is coupled to the robot plate. More particularly, a surface of the sterile connector 1006 (e.g., 1006I1, 1006I3) through which a connector (e.g., first component connector 1022, first signal connector 1023) can extend can abut a counterpart surface of the robot plate (e.g., 1004O1, 1004O2) through which a counterpart connector (e.g., component connector 1044, signal connector 1050) can extend. In some embodiments one or more of these surfaces (e.g., a surface through which a component connector or a signal connector extends) can be a planar surface.

The sterile connector 1006 can be locked to the robot plate 1004 such that relative movement between the sterile connector and the robot plate can be restricted. The lock 1030 of the sterile connector 1006 can be moved to the lock position such that the sterile connector cannot be removed or separated from the robot plate 1004. With the locking shaft 1030B engaged with the lock receptacle 1042, the lock handle 1030A can be moved from the unlocked position to the locked position. In some embodiments, the lock handle 1030A can be turned or rotated (e.g., by about 30 degrees, 45 degrees, 90 degrees, etc.) which can bring the lock handle into the vertical or substantially vertical lock position. The sterile drape 1010 can be draped over at least a portion of the robot arm 102 (see FIG. 1). In this manner, the sterile drape 1010 and the sterile connector 1006 can create a sterile barrier around at least a portion of the robot arm 102 such that the robot arm can be brought into a sterile surgical field without jeopardizing sterility of the field.

Figure 19:
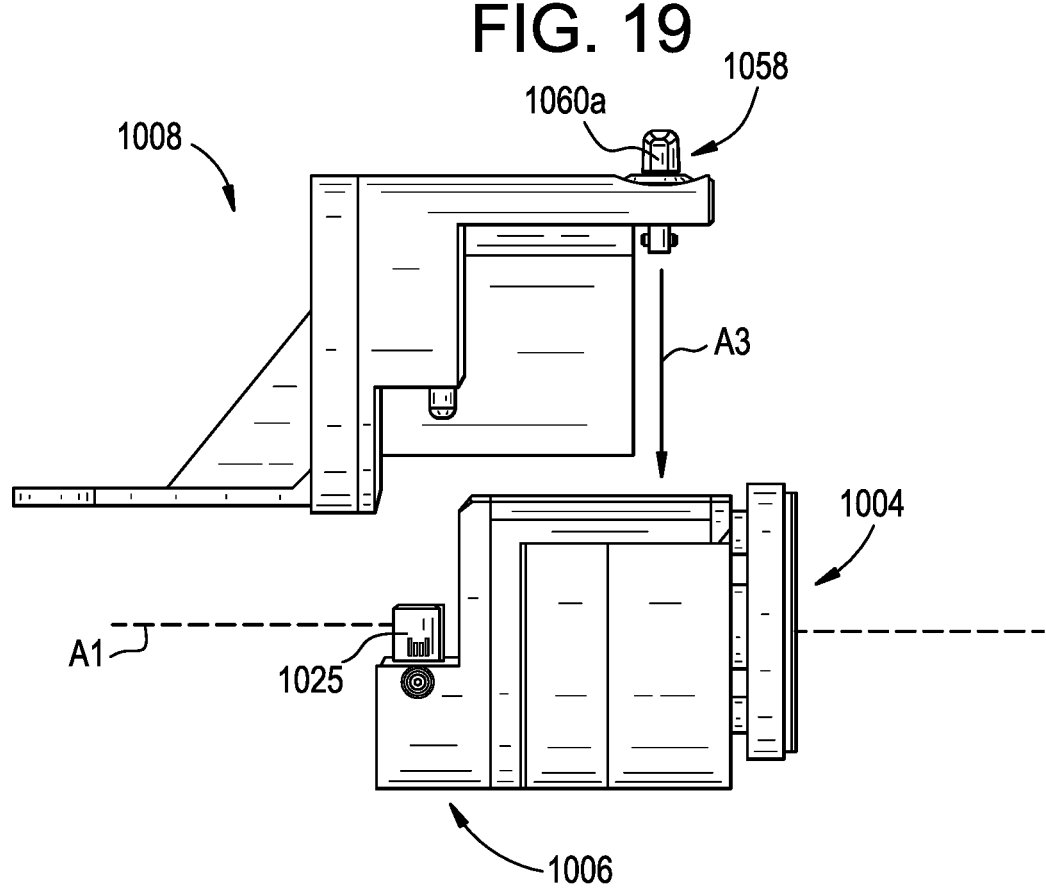
FIG. 19 illustrates a step in one embodiment of coupling the end effector of FIG. 9 to the sterile connector of FIG. 9.

FIG. 19 illustrates an embodiment of coupling the end effector 1008 to the sterile connector 1006. As shown in FIG. 19, the sterile connector 1006 can be coupled and locked to the robot plate 1004 prior to the end effector 1008 coupling to the sterile connector. The end effector 1008 can be coupled to the sterile connector 1006 along a radial insertion axis, e.g., the axis A3. In some embodiments, the insertion axis A3 of the end effector 1008 can extend transverse to, and, in some instances, orthogonal to, the insertion axis A2 of the sterile connector 1006. In some embodiments, the axis A3 can extend transverse to the central longitudinal axis A1 with a trajectory that can match an intended insertion trajectory of a surgical tool or instrument to be used during the surgical procedure. By way of non-limiting example, the insertion axis A3 of the end effector 1008 can extend at an angle of about 45 degrees, about 60 degrees, or about 90 degrees relative to the central longitudinal axis A1. Coupling the end effector 1008 to the sterile connector 1006 along an intended tool insertion axis can reduce the risk that the instrument or tool can fall on the patient or otherwise make unintended contact with the patient or other components in the surgical field.

The end effector 1008 can be moved towards the sterile connector 1008 along the axis A3 with the end effector's lock 1060 in the unlocked position. As shown in FIG. 19, in some embodiments, the lock handle 1060A can extend with a substantially horizontal orientation (i.e., substantially perpendicular to the central longitudinal axis A1) in the unlocked position. The end effector 1008 can be moved radially relative to the sterile connector 1006 such that the locking shaft 1060B of the lock 1060 can be inserted into the lock receptacle 1032 of the sterile connector's second connector component 1024 radially along the axis A3. The end effector signal connector 1064 can be inserted radially into the sterile connector's second signal connector 1025 along the axis A5. As introduced above, coupling the end effector 1008 to the sterile connector 1006 can prevent removal of the sterile connector from the robot plate 1004. More particularly, the end effector extension 1008A can act as a mechanical block and can prevent the sterile connector's first component connector 1022 from being placed in the unlocked position. Accordingly, the end effector 1008 can be coupled to the sterile connector 1006 such that the sterile connector and the sterile drape 1010 cannot be removed.

In some embodiments, one or more surfaces of the sterile connector 1006 can abut one or more surfaces of the end effector 1008 when the sterile connector is coupled to the end effector. More particularly, a surface of the sterile connector 1006 (e.g., 1006O2, 1006O3) through which a connector (e.g., second component connector 1024, second signal connector 1025) can extend can abut a counterpart surface of the end effector (e.g., 1008I1, 1008I2) through which a counterpart connector (e.g., component connector 1058, signal connector 1064) can extend. In some embodiments one or more of the surfaces (e.g., a surface through which a component connector or a signal connector extends) can be a planar surface.

The end effector 1008 can be locked to the sterile connector 1006 such that relative movement between the end effector and the sterile connector can be restricted. The lock 1060 of the end effector 1008 can be moved to the lock position such that the end effector cannot be removed or separated from the sterile connector 1006. The lock handle 1060A can be moved from the unlocked position to the locked position with the locking shaft 1060B received within the lock receptacle 1034. In some embodiments, the lock handle 1060A can be rotated or turned from the unlocked position to bring the lock into the locked position in which the lock handle can extend parallel or substantially parallel to the central longitudinal axis A1 (see FIG. 9). Accordingly, the end effector 1008 can be securely locked to the sterile connector 1006.

If a surgical instrument or instrument guide is not integrally formed with, or already connected to, the end effector 1008, such a surgical instrument or guide can be inserted into the end effector instrument mount 1056. In some embodiments, the surgical procedure can require a "hot swap" of end effectors, in which the end effector 1008 can be removed from the sterile connector 1006 and can be replaced by a second end effector 1008' (such as, for example, any one of the end effectors shown in FIGS. 6-8). In other instances, the end effector 1008 can remain coupled and locked to the sterile connector 1006 and an instrument received within a guide or the instrument mount 1056 of the end effector can be removed and replaced with a second instrument. The surgical robotic system 1000 can maintain sterility of the surgical field during the hot swap of end effectors or surgical instruments. In other words, the sterile barrier around the robot arm that can be established by the sterile drape 1010 can remain intact during the hot swap such that a need for re-draping and/or re-sterilizing the robot arm can be eliminated during the course of the surgical procedure.

To facilitate a swap of end effectors, the lock 1060 of the end effector's component connector 1058 can be moved from the locked position to the unlocked position such that the end effector 1008 can be separated from the sterile connector 1006. The end effector 1008 can be moved away from the sterile connector 1006 along the radial axis A3. The second end effector 1008' can be coupled and locked to the sterile connector 1006 in a similar manner as described above with respect to the end effector 1008.

Figure 9:
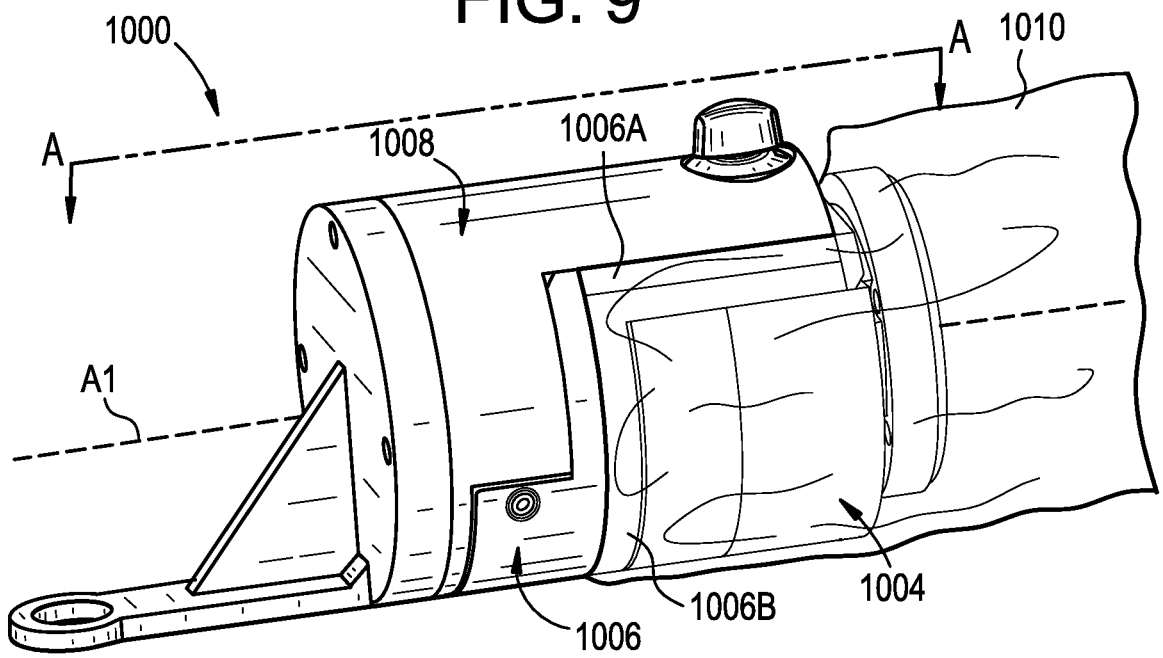
FIG. 9 is a perspective of another embodiment of a surgical robotic system including a robot plate, a sterile connector, and an end effector in an assembled configuration.
Figure 20:
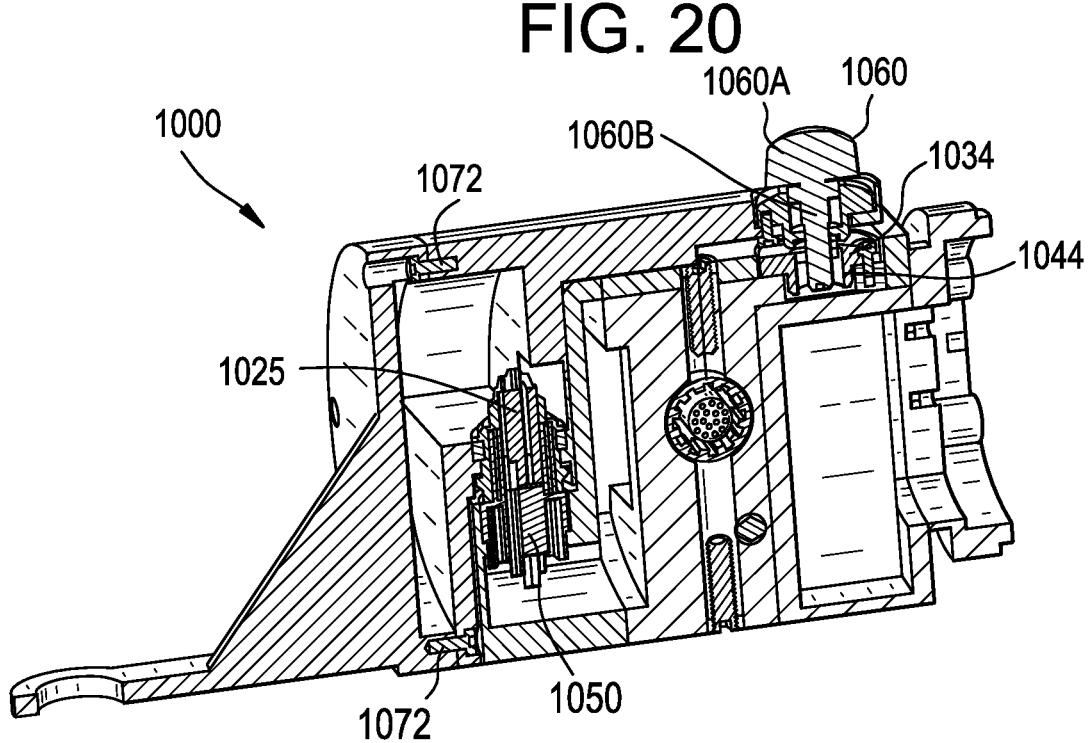
FIG. 20 is a cross-sectional view of the surgical robotic system of FIG. 9 taken along the line A-A of FIG. 9.
Figure 21:
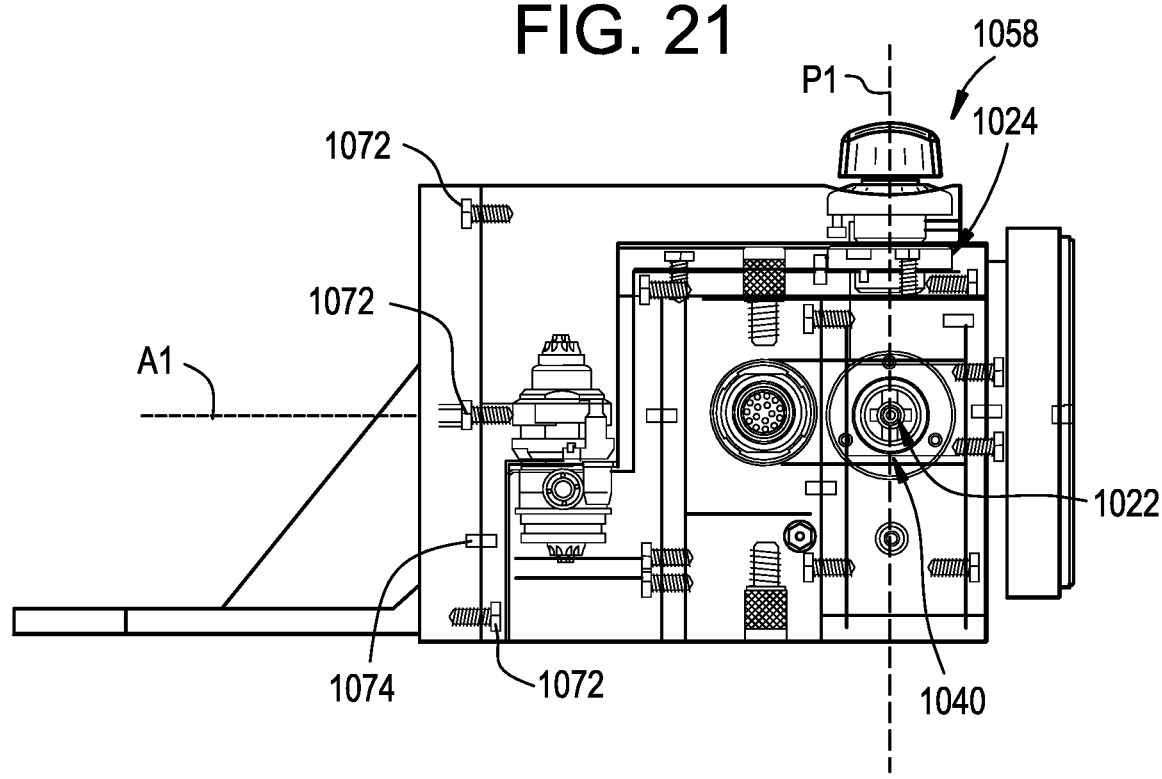
FIG. 21 is a partially-transparent side view of the surgical robotic system of FIG. 9.

With the sterile connector 1006 coupled and locked to the robot arm 1004 and the end effector 1008 coupled and locked to the sterile connector, the robotic surgical system 1000 can be brought into its fully assembled configuration, as shown in FIGS. 9 and 10. FIGS. 20 and 21 show additional views of the assembled robotic surgical system 1000. FIG. 20 is a cross-sectional view of the system 1000 taken along the line A-A in FIG. 9. FIG. 21 shows the system 1000 with partially transparent components (robot plate 1004, sterile connector 1006, end effector 1008) such that internal connections between the components can be seen. For example, the physical component connection between the end effector 1008 and the sterile connector 1006 can be seen with the end effector lock 1060 received within the sterile connector lock receptacle 1034. More particularly, the locking shaft 1060B can be received within the slot of the lock receptacle 1034, and the lock handle 1060A can be placed in the locked position. The signal connection between the end effector signal connector 1064 and the sterile connector second signal connector 1025 can also be seen, which can establish a signal transmission path between the end effector 1008 and the sterile connector 1006. The physical component connection and the signal connection between the sterile connector 1006 and the robot plate 1004 can also be seen, and can extend radially between the sterile connector and the robot plate. In some embodiments, the physical component connection between the sterile connector 1006 and the robot plate 1004 (i.e., the sterile connector first component connector 1022 and the robot plate component connector 1040) and the physical component connection between the sterile connector and the end effector 1008 (i.e., the sterile connector second component connector 1024 and the end effector component connector 1058) can be aligned or substantially aligned along the longitudinal axis A1 of the robotic surgical system. In other words, the physical component connections can lie within a single plane P1 perpendicular to the longitudinal axis A1. Such alignment of the physical component connections can minimize an overall axial length (e.g., as viewed along longitudinal axis A1) of the system 1000, as compared to a configuration with axially offset physical component connections. FIGS. 20 and 21 also show additional mechanical connectors of the individual components, such as screws 1072 and pin 1074 that can hold the end effector 1008 together. Similar pins and screws are visible within the sterile connector 2006 and the robot plate 2004 as well.

In some embodiments, the signal connectors, i.e., the sterile connector's first signal connector 1023 and second signal connector 1025, the robot plate's signal connector 1050, and the end effector's signal connector 1064, can establish signal transmission paths and can transmit electrical signals, such as, for example, power, data, command instructions, etc., between the robot plate 1004, the sterile connector 1006, and the end effector 1008. For example, coupling of two signal connectors, e.g., the sterile connector's first signal connector 1023 to the robot plate's signal connector 1050, can establish a physical transmission path for signals to pass between the sterile connector 1006 and the robot plate 1004. Moreover, a printed circuit board (shown in FIG. 3) can be integrated into one or more of the components to provide additional signal transmission and user interaction capability. In some embodiments, the sterile connector can include a force sensor that can measure and transmit data to a user regarding force being applied to the robot plate. By way of non-limiting example, signal transmission associated with the robotic surgical system 1000 can include one or more of the following: power can be transmitted through the robot arm, via the robot plate 1004 and the sterile connector 1006, to the end effector 1008 to power the end effector and/or a surgical instrument associated therewith; a user can control movement of the robot arm through input into the user interface 1018 on the sterile connector, either before or after the end effector is coupled with the sterile connector; a user can input instructions for movement or operational control of the end effector into the user interface 1018 on the sterile connector; robotic system status data can be transmitted to a user, such as, for example, a position of the sterile connector lock 1030 and/or the end effector lock 1060, a status of contact between surfaces of the sterile connector, robot plate, and/or end effector, a status of the sterile barrier around the robot arm, absolute position information of a surgical instrument of the end effector, relative position information of the surgical instrument of the end effector as related to the surgical field and/or allowable instrument boundaries.

Additionally, or alternatively, one or more of the end effector 1008, the sterile connector 1006, and the robot plate 1004 can include wireless communication technology. For example, in some embodiments a user can be notified when the end effector 1008, 1008' is coupled and locked to the sterile connector 1006. Moreover, in some embodiments, the end effector 1008, 1008' can be registered with the robotic surgical system 1000, and information regarding the end effector 1008, 1008' can be transmitted to the user. By way of non-limiting example, the end effector 1008, 1008' can include a Bluetooth Low Energy (BLE) or radio-frequency identification (RFID) tag which can be registered by a BLE or RFID reader that can be placed within the sterile connector 1006 and/or robot plate 1004. Identification data can be received by the BLE or RFID reader and can be transmitted to the user via the user interface 1018 or other connected component (e.g., a wireless device, a computing station, etc.) during the surgical procedure. The data provided by the end effector 1008, 1008' and transmitted by the sterile connector 1006 can provide information on which version of the end effector is attached to the sterile connector, including, for example, dimensions and capabilities of the end effector. Additionally, or alternatively, the sterile connector 1006 can transmit identification data regarding the sterile connector (e.g., through a BLE tag, RFID tag, a wired communication channel within the sterile connector, etc.) to the user via the user interface 1018 or other connected component. Identification information that can be obtained about the end effector and/or sterile connector can allow for tracking of the components by navigational tracking systems and/or can provide for understanding of unique component configurations, such as, for example, a configuration of buttons or other user interface components on the sterile connector and their associated operational capabilities. While certain examples of passing signals through wireless transmission are provided for herein, in some instances, it can be advantageous to pass such signals through one or more physical signal transmission paths. For example, transmitting signals along a physical (i.e., wired) path can allow for increased signal transmission speed and/or bandwidth, can provide for improved data security, and can allow for transmission of greater amounts of power. As discussed above, the coupling of counterpart signal connectors (e.g., the sterile connector's first signal connector 1023 to the robot plate signal connector 1064, the sterile connector's second signal connector 1025 to the end effector signal connector 1064) can establish a physical transmission path between the components associated with the coupled signal connectors.

Figure 22:
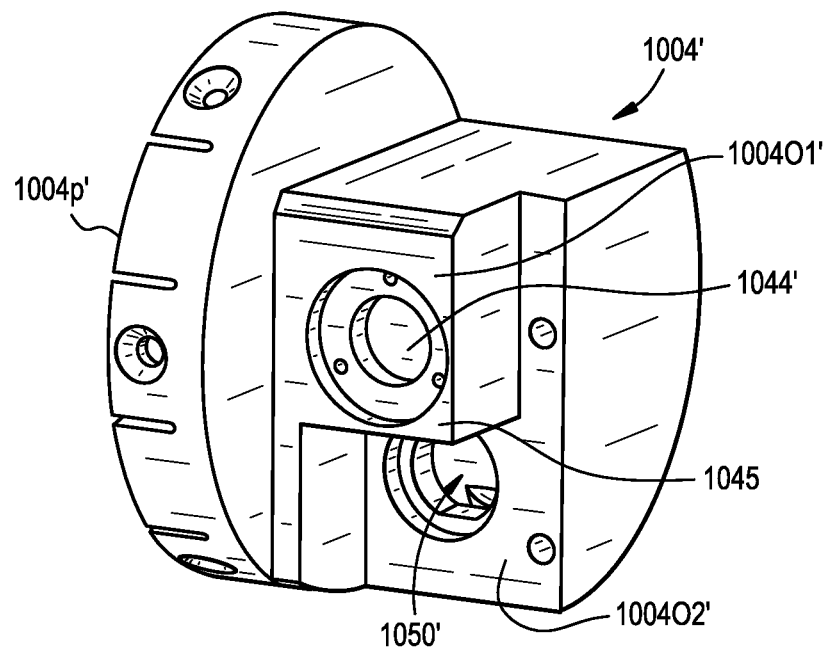
FIG. 22 is a perspective view of another embodiment of a robot plate of the present disclosure.
Figure 23:
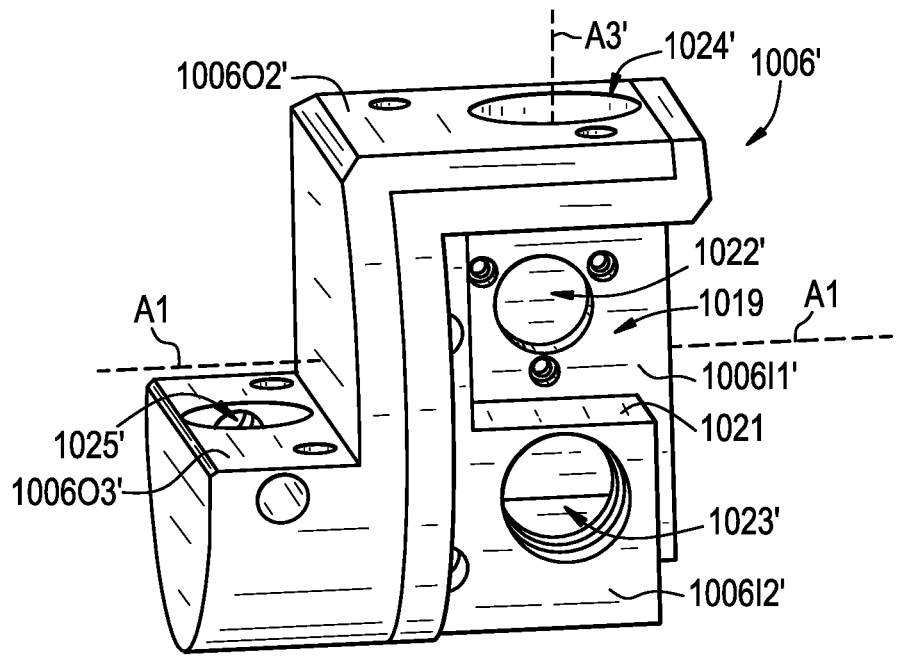
FIG. 23 is a perspective view of another embodiment of a sterile connector of the present disclosure.
Figure 24:
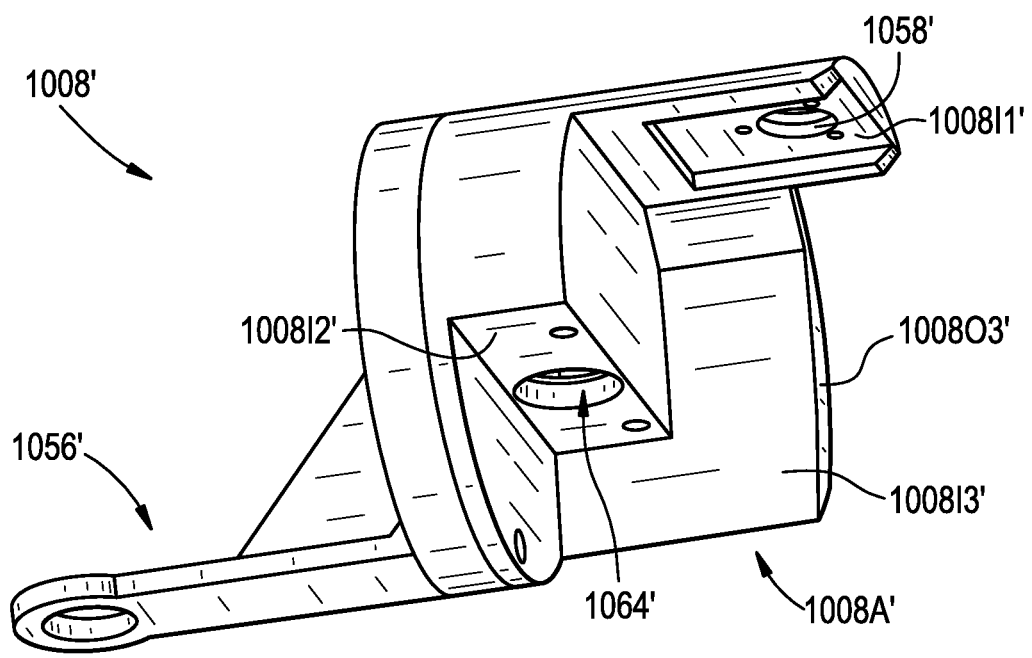
FIG. 24 is a perspective view of another embodiment of an end effector of the present disclosure.

FIGS. 22-24 illustrate an alternative construction of components of the robotic surgical system 1000. More particularly, FIGS. 22-24 show a robot plate 1004', a sterile connector 1006', and an end effector 1008', respectively, with a more compact configuration such that an axial length of the robotic surgical system 1000 can be reduced. Except as indicated below, the structure, operation, and use of this embodiment is similar or identical to that of the robotic surgical system 1000. Accordingly, a detailed description of said structure, operation, and use is omitted here for the sake of brevity.

The sterile connector 1006' can include a first component connector 1022', a second component connector 1024', a first signal connector 1023', and a second signal connector 1025', each of which can have the same construction and function as described with reference to the sterile connector 1006 above. The first component connector 1022' and the first signal connector 1023, however, can have a reduced longitudinal distance, as measured along the central longitudinal axis A1, extending therebetween. In some embodiments, the first component connector 1022' and the first signal connector 1023' can be substantially longitudinally aligned along the central longitudinal axis A1. For example, in some embodiments the first component connector 1022' can be located substantially above the central longitudinal axis A1 and the first signal connector 1023' can be located substantially below the central longitudinal axis such that the first component connector and the first signal connector can have a "stacked" orientation. Further, in some embodiments, the first signal connector 1023' can extend through an inner surface 1006I2' that can be formed on a stepped extension 1021. The stepped extension 1021 can extend radially inward from a portion of the first inner surface 1006I1' through which the first component connector 1022' can extend, such that the first component connector and the first signal connector 1023' can be substantially longitudinally aligned.

The robot plate 1004' can include a component connector 1044' and a signal connector 1050'. The robot plate 1004' can have a complementary geometry to that of the sterile connector 1006' such that the component connector 1044' and the signal connector 1050' can couple with the sterile connector's first component connector 1022' and first signal connector 1023', respectively. More particularly, the component connector 1044' and the signal connector 1050' can have a reduced longitudinal distance extending therebetween, as compared to the robot plate 1004 described above, which can enable coupling with the counterpart features on the sterile connector 1006'. For example, in some embodiments, the component connector 1044' can be located substantially above the central longitudinal axis A1 and the signal connector 1050' can be located substantially below the central longitudinal axis such that the component connector and the signal connector can have a "stacked" orientation. Further, in some embodiments, the component connector 1044' can extend through an outer surface 1004O1' that can be formed on an extension 1045. The extension 1045 can extend radially from an outer surface 1004O2' through which the signal connector 1050' can extend. When the robot plate 1004' is coupled with the sterile connector 1006', the extension 1045 of the robot plate can be received within a recessed portion 1019 that can be formed by the extension 1021 of the sterile connector 1006'.

FIG. 24 illustrates the end effector 1008', which can include a component connector 1058' and a signal connector 1064', each of which can have the same construction and function as described with reference to the end effector 1008 above. An extension 1008A' of the end effector 1008' can have the same purpose and function as that of the extension 1008A described above, but can have a reduced axial length. This is because the reduced axial length of the sterile connector 1006' can result in a reduced required axial length of the extension 1008A' in order for the extension to act as a mechanical stop to movement of a lock of the sterile connector's first component connector 1022'.

Figure 25:
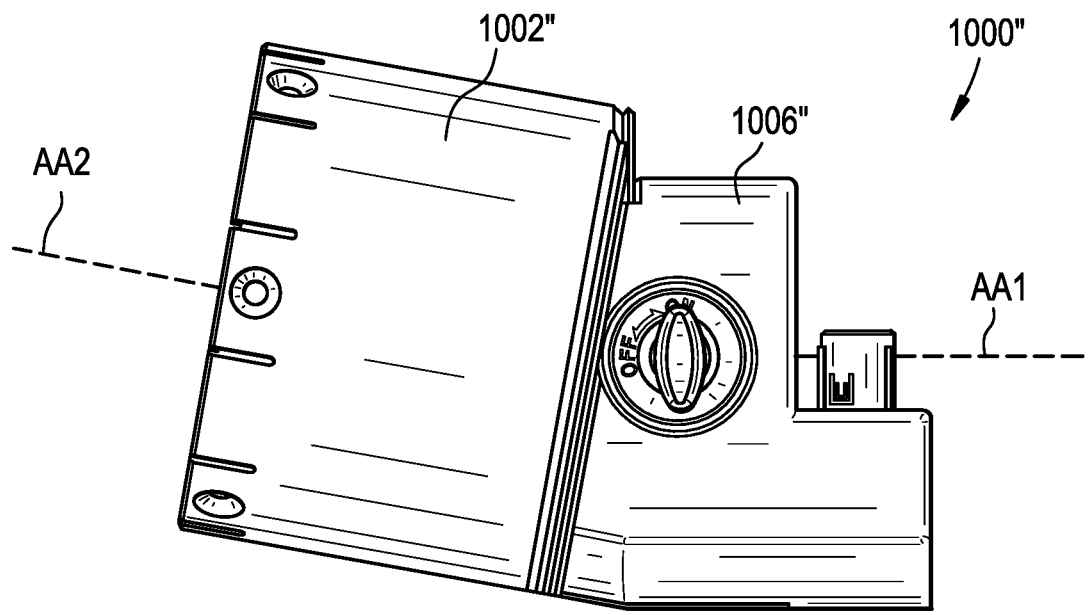
FIG. 25 is a perspective view of another embodiment of a robot plate and a sterile connector in an assembled configuration.
Figure 26:
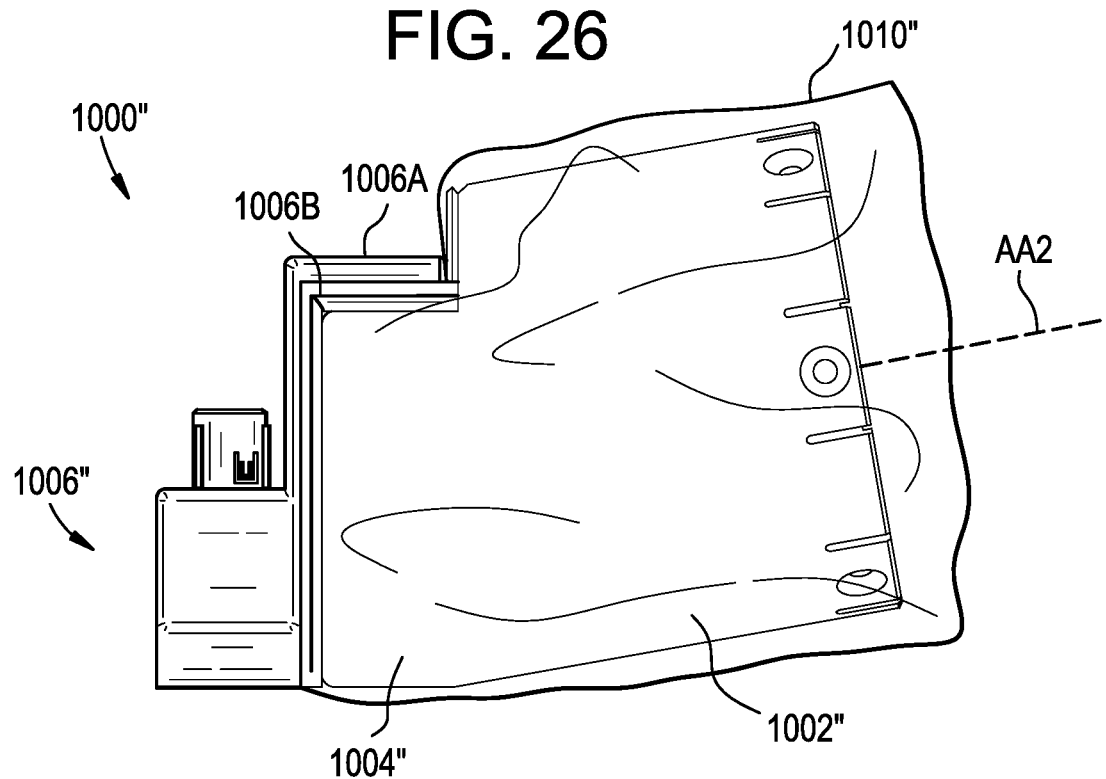
FIG. 26 is another perspective view of the assembled configuration of FIG. 25 with a sterile drape.

FIGS. 25-32 illustrate another embodiment of the robotic surgical system 1000. FIGS. 25 and 26 show a robotic surgical system 1000" in a partially assembled configuration with a sterile connector 1006" coupled with, and locked to, a robot plate 1004". The robot plate 1004" can be integrally formed with a robot arm 1002". In other words, the robot plate 1004" can be an integrally formed distal-most joint or portion of the robot arm 1002". The sterile connector 1006" can couple with the robot plate 1004" such that the sterile connector can extend distally along a central longitudinal axis AA1 at an oblique angle relative to a central longitudinal axis AA2 of the robot arm 1002". In some embodiments, the central longitudinal axis AA1 of the sterile connector 1006" can be co-axial with a central longitudinal axis AA3 (FIG. 28) of the robot plate 1004". As discussed in detail below with reference to FIGS. 27-32, the robot plate 1004" and the sterile connector 1006" can each include one or more counterpart surfaces that can align with one another when in the assembled configuration and can facilitate a transition from the robot arm 1002" extending along the axis AA2 to the sterile connector 1006" extending along the axis AA1.

The sterile connector 1006" can include a sterile drape 1010". In some embodiments, the sterile drape 1010" can be sandwiched between a first portion 1006A" of the sterile connector and a second portion 1006B" of the sterile connector. The sterile connector 1006" can be coupled to the robot plate 1004" such that the sterile drape 1010" can extend over the robot plate 1004" and at least a portion of the robot arm 1002" and can create a sterile barrier around the robot plate and the robot arm. While not shown in FIGS. 25 and 26, any of the end effectors disclosed herein can be coupled with the sterile connector 1006" as described above with reference to the end effectors 1008, 1008'. Except as indicated below, the structure, operation, and use of this embodiment is similar or identical to that of the robotic surgical system 1000. Accordingly, a detailed description of said structure, operation, and use is omitted here for the sake of brevity.

Figure 27:
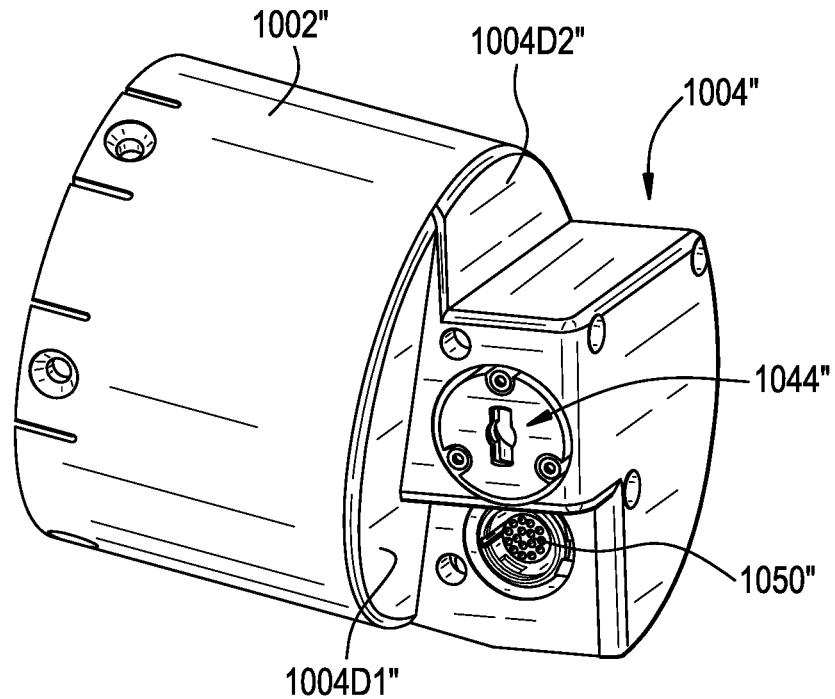
FIG. 27 is a perspective view of the robot plate of FIG. 25.
Figure 28:
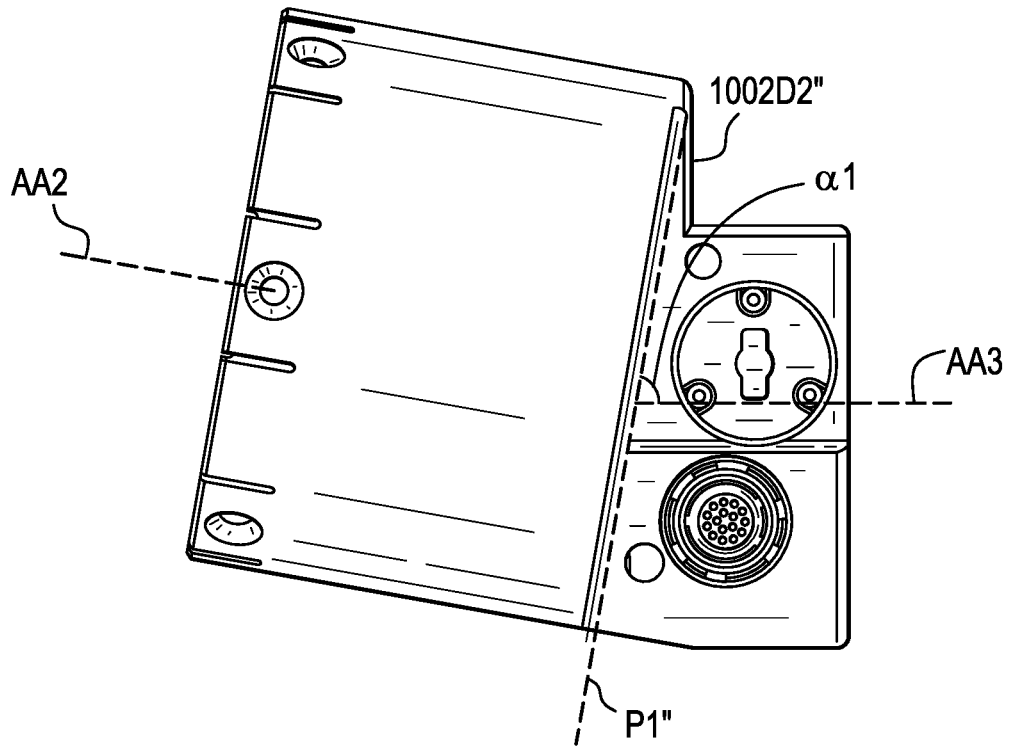
FIG. 28 is a lateral view of the robot plate of FIG. 25.
Figure 29:
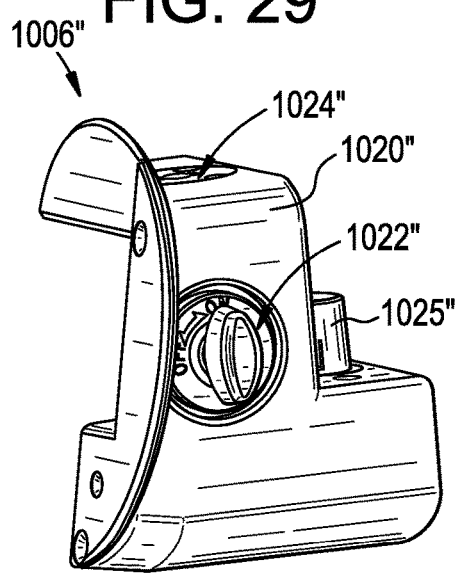
FIG. 29 is a perspective view of the sterile connector of FIG. 25.
Figure 30:
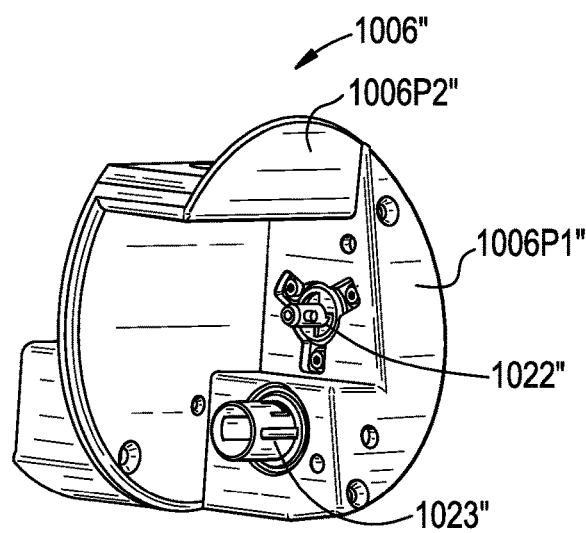
FIG. 30 is another perspective view of the sterile connector of FIG. 25.
Figure 31:
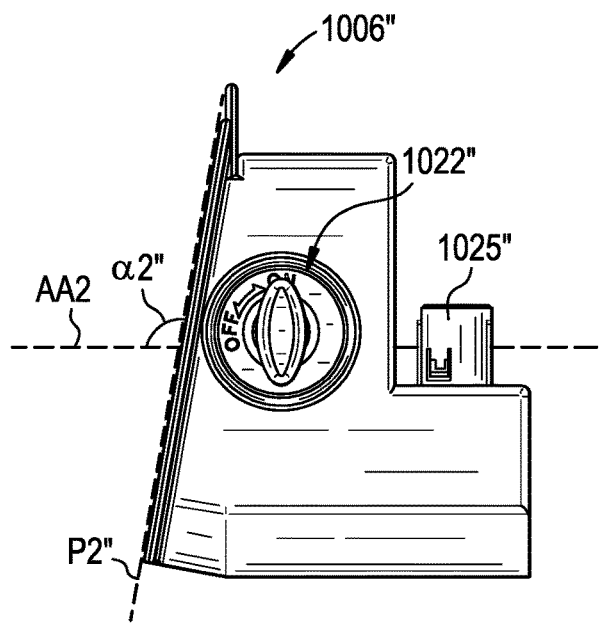
FIG. 31 is a lateral view of the sterile connector of FIG. 25.
Figure 32:
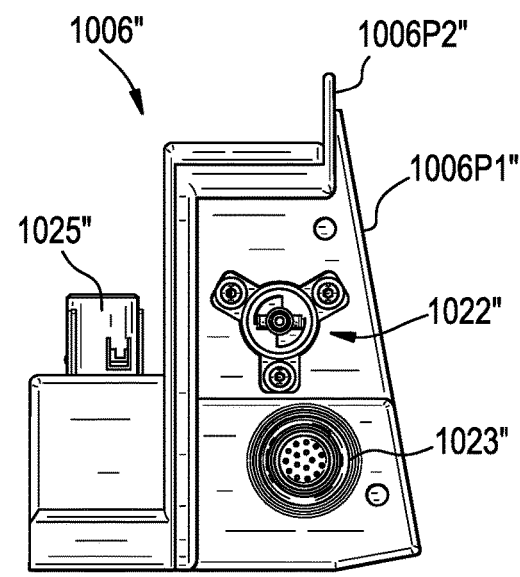
FIG. 32 is another lateral view of the sterile connector of FIG. 25.

FIGS. 27 and 28 show a perspective view and a lateral view, respectively, of the robot plate 1004" integrally formed with the robot arm 1002". The robot plate 1004" can extend along the central longitudinal axis AA3 and can include a component connector 1044" and a signal connector 1050". The central longitudinal axis AA3 of the robot plate 1004" can extend at an oblique angle relative to the central longitudinal axis AA2 of the robot arm 1002". In some embodiments, a first distal-facing transition surface 1004D1" can extend along a plane P1" at an oblique angle α1" relative to the central longitudinal axis AA3 of the robot plate 1004". Further, in some embodiments, a second distal-facing transition surface 1004D2" can extend perpendicular to the central longitudinal axis AA3 of the robot plate 1004".

The sterile connector 1006" will now be described in greater detail with reference to FIGS. 29-32. The sterile connector 1006" can include a first component connector 1022" that can couple the sterile connector to the robot plate 1004", a second component connector 1024" that can couple the sterile connector to the end effector (e.g., 1008, 1008'), a first signal connector 1023" that can transmit signals between the sterile connector and the robot plate, and a second signal connector 1025" that can transmit signals between the sterile connector and the end effector as discussed in detail above. Except as described herein, construction of the sterile connector 1006" and assembly of the sterile connector with the robot plate 1004" and end effector 1008, 1008' can be similar or identical to that of the sterile connectors 1006, 1006' described above.

The sterile connector 1006" can have a body 1020" with a proximal-facing transition surface 1006P1" that can extend along a plane P2" at an oblique angle α2" relative to the central longitudinal axis AA3 of the sterile connector. The proximal-facing transition surface 1006P1" can have a counterpart geometry to the distal-facing transition surface 1004D1" of the robot plate 1004" such that when the sterile connector 1006" is coupled to the robot plate the proximal-facing surface of the sterile connector can align with and abut the distal-facing transition surface of the robot arm. For example, the angle α2" of the proximal-facing surface 1006P1" can be supplementary to the angle α1" of the distal-facing transition surface 1004D1". In this manner, an interface between these two surfaces can facilitate a transition between the robot arm 1002" and the sterile connector 1006" and can align the central longitudinal axes AA2, AA3 of the sterile connector and the robot plate 1004" in the assembled configuration (FIGS. 25 and 26). The sterile connector 1006" can have a second proximal-facing transition surface 1006P2" that can have a counterpart geometry to the second distal-facing transition surface 1006D2". For example, in some embodiments the second proximal-facing transition surface 1006P2" can extend perpendicular to the central longitudinal axis AA3 of the sterile connector.

Figure 33:
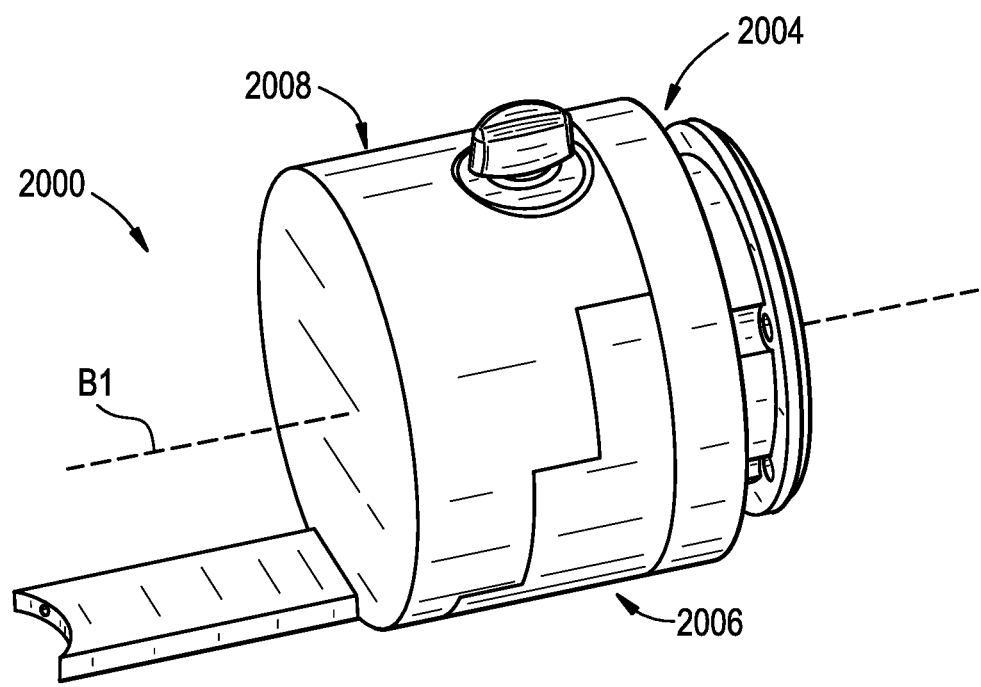
FIG. 33 is a perspective view of another embodiment of a surgical robotic system including a robot plate, a sterile connector, and an end effector in an assembled configuration.

FIGS. 33-37 illustrate another embodiment of a robotic surgical system 2000. FIG. 33 shows an assembled robotic surgical system 2000, which can extend along a central longitudinal axis B1 and can include a robot plate 2004, a sterile connector 2006, and an end effector 2008. A sterile drape can extend from the sterile connector 2006 and can drape the robot plate 2004 and at least a portion of the robot arm (see FIG. 1). In this embodiment, the sterile connector 2004 can axially couple to the robot plate 2004. Furthermore, the end effector 2008 can be coupled to the sterile connector 2004 such that access to a first component connector 2022 of the sterile connector can be blocked, and removal of the sterile connector from the robot plate 2004 can be prevented. Except as indicated, the structure, operation, and use of this embodiment is similar or identical to that of the robotic surgical system 1000. Accordingly, a detailed description of said structure, operation, and use is omitted here for the sake of brevity.

The sterile connector 2006 can include a body 2020, a first component connector 2022 that can couple and lock the sterile connector to the robot plate 2004, and a second component connector 2024 that can couple and lock the sterile connector to the end effector 2008. The first component connector 2022 can extend axially through the body 2020, i.e., along an axis B2 that can be parallel to the central longitudinal axis B1. The first component connector 2022 can include a lock 2026, such as a quarter-turn lock with a lock handle 2026A and a locking shaft 2026B, that can be moved between a first locked position and a second unlocked position. The first component connector 2022 can extend from a distal-facing surface 2006D1 of the body 2020 to a proximal-facing surface 2006P1. The lock handle 2026A can extend distally from the distal-facing surface 2006D1 such that the lock handle can be accessed by a user. The locking shaft 2026B can extend proximally from the proximal-facing surface 2006P1. In some embodiments, the lock handle 2026A can be received within a recessed portion 2028 of the body 2020. The recessed portion 2028 can longitudinally offset the first distal-facing surface 2006D1 through which the lock 2026 can extend from a second distal-facing surface 2006D2 of the sterile connector 2006. The recessed portion 2028 can be dimensioned such that a user can move the lock 2026 between the first locked position and the second unlocked position. In some embodiments, the recessed portion 2028 can be generally cylindrical in shape with an inner surface 2006I1. As discussed in detail below, the end effector 2008 can be coupled to the sterile connector 2006 such that access to the embedded lock 2026 can be prevented. In other words, the lock 2026 can be "embedded" within the sterile connector 2006 such that access to the lock handle 2026A can be prevented in the fully assembled configuration of the robotic surgical system 2000.

The second component connector 2024 of the sterile connector 2006 can extend from an outer-facing surface 2006O1 through the body 2020 along an axis B3. The axis B3 can extend transverse to the central longitudinal axis B1, and, in some embodiments, can extend orthogonal to the central longitudinal axis. The second component connector 2024 can be configured to receive a counterpart component connector 2044 of the end effector 2008. In some embodiments, the second component connector 2024 can include a lock receptacle 2030 that can receive a lock, as described above with reference to the robotic surgical system 1000.

Figure 34:
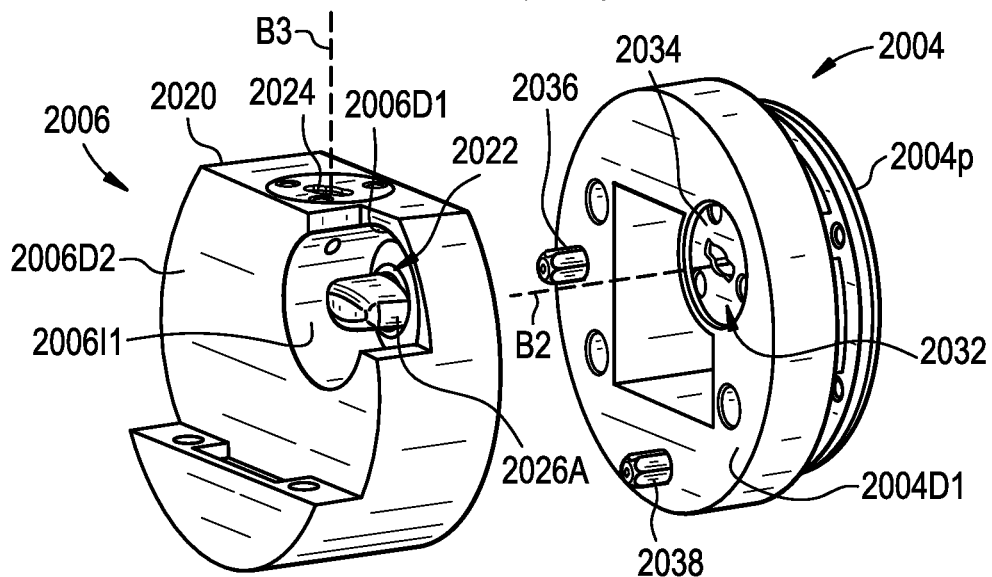
FIG. 34 illustrates a step in one embodiment of coupling the sterile connector of FIG. 26 to the robot plate of FIG. 33.
Figure 35:
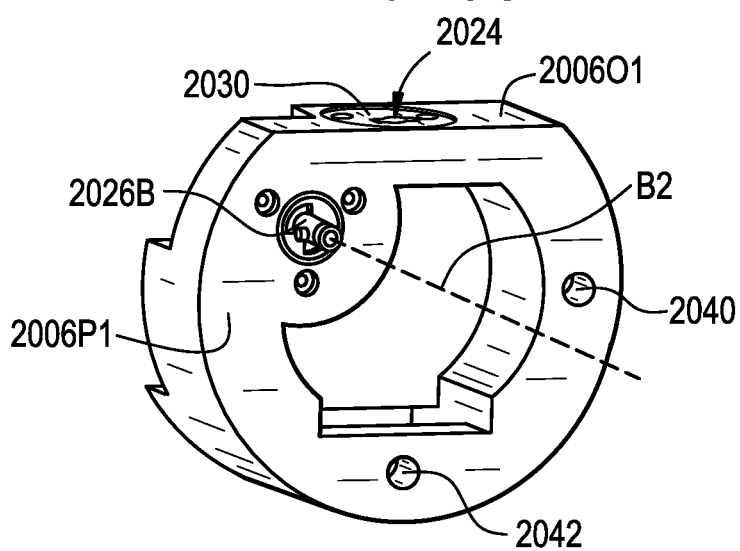
FIG. 35 is a perspective view of the sterile connector of FIG. 33.

With reference to FIG. 34, the sterile connector 2006 can be moved axially along the central longitudinal axis B1 towards the robot plate 2004 such that the first component connector 2022 can engage with a component connector 2032 of the robot plate 2004. More particularly, the locking shaft 2026B of the sterile connector 2006 can be inserted into a lock receptacle 2034 of the robot plate component connector 2022. The lock receptacle 2034 can extend proximally into the robot plate 2004 from a distal-facing surface 2004D1 along an axis B2 that can be parallel to the central longitudinal axis B1. The lock 2030 can be moved from the unlocked second position in which the sterile connector can be separated from the robot plate 2004 to the locked first position, as discussed above. In some embodiments, the robot plate 2004 can include one or more alignment pins 2036, 2038 that can extend distally from the distal-facing surface 2004D1. The pins 2036, 2038 can be received within corresponding pin recesses 2040, 2042, respectively, that can extend into the body 2020 from the proximal facing surface 2006P1.

Figure 36:
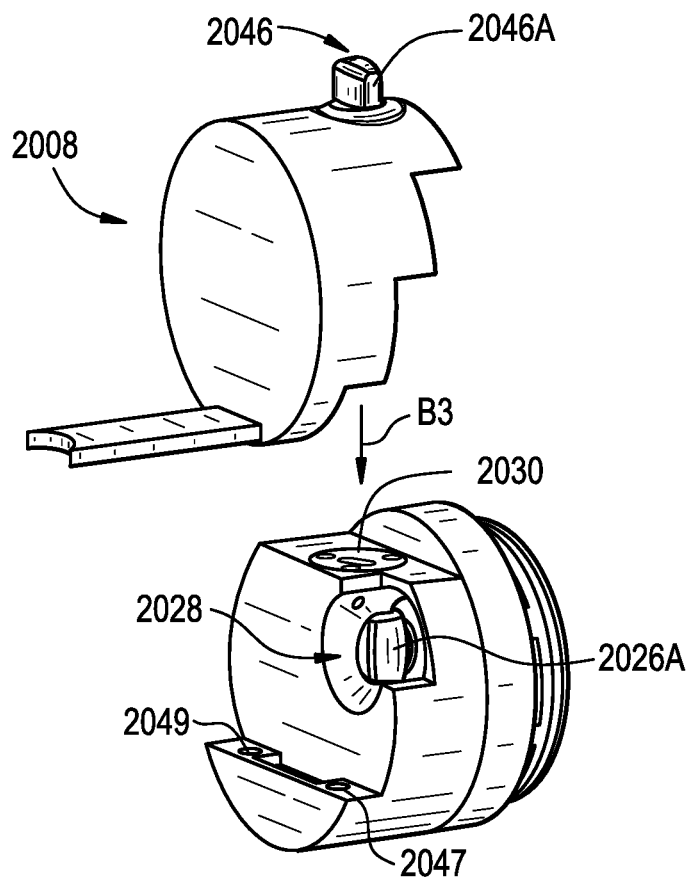
FIG. 36 illustrates a step in one embodiment of coupling the end effector of FIG. 33 to the sterile connector of FIG. 33.
Figure 37:
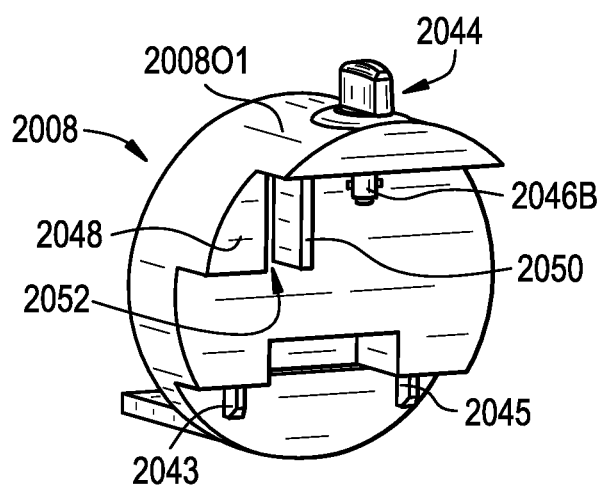
FIG. 37 is a perspective view of the end effector of FIG. 33.
Figure 38:
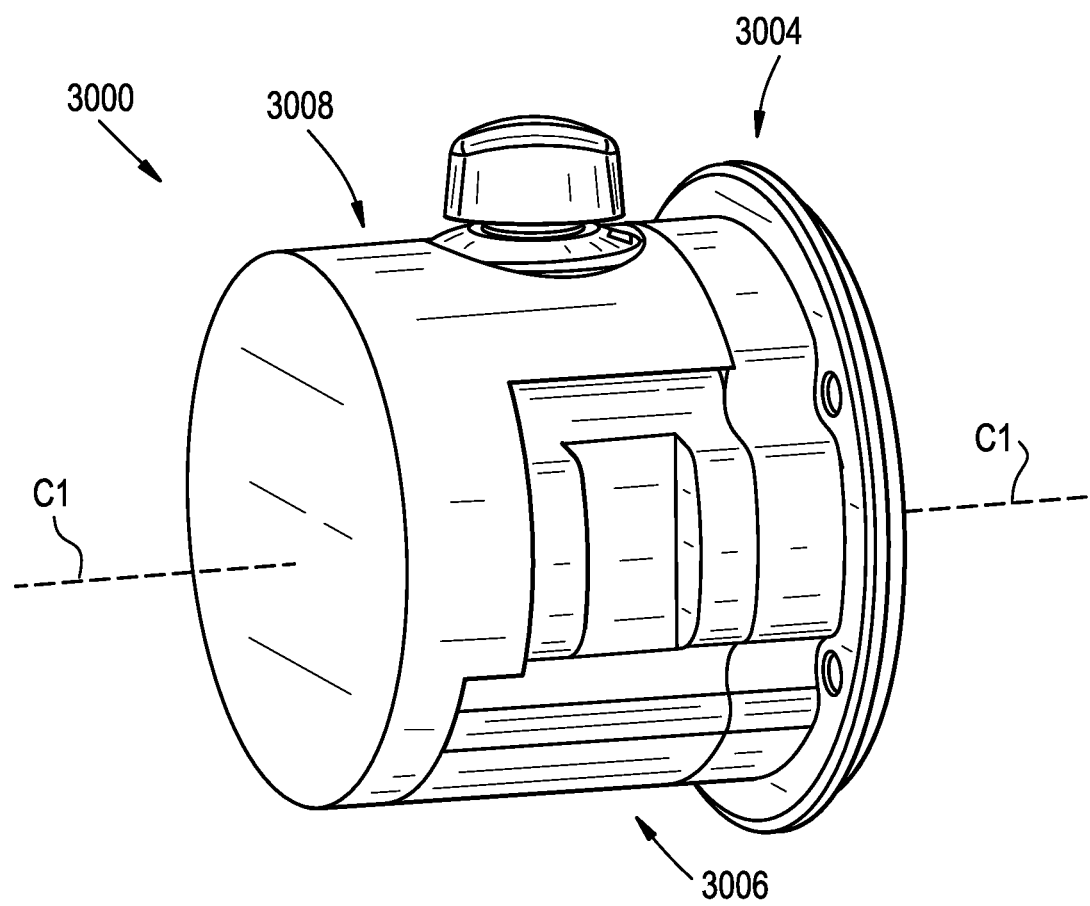
FIG. 38 a perspective view of another embodiment of a surgical robotic system including a robot plate, a sterile connector, and an end effector in an assembled configuration.

With reference to FIGS. 36 and 37, the end effector 2008 can be coupled to the sterile connector 2006. The end effector 2008 can be moved radially towards the sterile connector along the axis B3. As discussed above, in some embodiments, the axis B3 can extend along an intended insertion trajectory of a surgical instrument. A component connector 2046 of the end effector 2008 can engage with the sterile connector's second component connector 2024 and can couple the end effector to the sterile connector 2006. More particularly, the end effector component connector 2046 can include a lock 2046, such as a quarter-turn lock having a lock handle 2046A and a locking shaft 2046B. The lock 2046 can extend from an outer surface 2008O1 of the end effector 2008 through an inner surface (not shown) along the axis B3. The locking shaft 2046B can be inserted into the lock receptacle 2030 of the sterile connector's second component connector 2024. The lock 2046 can then be moved by a user from the unlocked position to the locked position and can lock the end effector 2008 to the sterile connector 2006. The end effector 2008 can include alignment pins 2043, 2045 that can be received within pin recesses 2047, 2049 of the sterile connector.

As introduced above, the end effector 2008 can be coupled to the sterile connector 2006 such that access to the first component connector 2022 can be prevented. To that end, a geometry of the end effector 2008 can complement a geometry of the sterile connector 2006 and can cover at least a portion of the lock 2026 such that the lock cannot be accessed by a user. In the fully assembled configuration of the robotic surgical system 2000 (see FIG. 26), the end effector 2008 can completely conceal the lock handle 2026A. Moreover, the end effector 2008 can be coupled to the sterile connector 2008 such that a first extension 2048 and a second extension 2050 of the end effector can be placed relative to the lock handle 2026A such that movement of the lock handle 2026A from the locked position can be restricted. For example, in the illustrated embodiment, the first extension 2048 and the second extension 2050 can have a gap 2052 formed therebetween. The gap 2052 can be sized such that the lock handle 2026A can be received therein when placed in the locked position. There can be insufficient space provided within the gap 2052, however, for the lock handle 2026A to move from the locked position to the unlocked position. Accordingly, the end effector 2008 can prevent unlocking of the sterile connector 2006 from the robot plate 2004 by eliminating access to the lock 2026 and by restricting movement of the lock 2026 from the locked position.

FIGS. 38-41 illustrate another embodiment of a robotic surgical system 3000, which can include a robot plate 3004, a sterile connector 3006, and an end effector 3008. A sterile drape (not shown) can extend from the sterile connector 3006 and can drape the robot plate 3004 and at least a portion of the robot arm (see FIG. 1). The robotic surgical system 3000 can extend along a central longitudinal axis C1. The sterile connector 3006 can be axially coupled to the robot plate 3004, i.e., along the central longitudinal axis C1. Except as indicated, the structure, operation, and use of this embodiment is similar or identical to that of the robotic surgical system 1000, 2000. Accordingly, a detailed description of said structure, operation, and use is omitted here for the sake of brevity.

The sterile connector 3006 can include a body 3020, a first component connector 3022, a second component connector 3024, and a third component connector 3026. The first and second component connectors 3022, 3024 can each be configured to engage with a counterpart component of the robot plate 3004 to couple and selectively lock the sterile connector 3006 to the robot plate. The third component connector 3026 can couple the sterile connector to the end effector. In the illustrated embodiment, the first component connector 3022 and the second component connector 3024 can each be a ball-lock pin that can engage with a counterpart lock pin receptacle 3028, 3030 of the robot plate 3004 to axially couple the sterile connector to the robot plate. The first pin 3022 can have a pin head 3022A and a pin locking shaft 3022B. The first pin 3022 can extend axially through the body 3020 from a distal-facing surface 3006D1 to a proximal-facing surface 3006P1. The pin head 3022A can face distally such that a user can access the pin head when the sterile connector 3006 is coupled with the robot plate 3004. The pin locking shaft 3022B can extend proximally from the proximal-facing surface 3006P1. The second ball-lock pin 3024 can have a pin head 3024A and a pin locking shaft 3024B and can extend through the body 3020 of the sterile connector in a similar manner to that of the first pin 3022.

The robot plate 3004 can include a first component connector 3028, i.e., the first lock pin receptacle and a second component connector 3030, i.e., the second lock pin receptacle. The first and second lock pin receptacle 3028, 3030 can each extend axially into the robot plate 3004 from a distal-facing surface 3004D1 towards a proximal-facing surface 3004P1.

Figure 39:
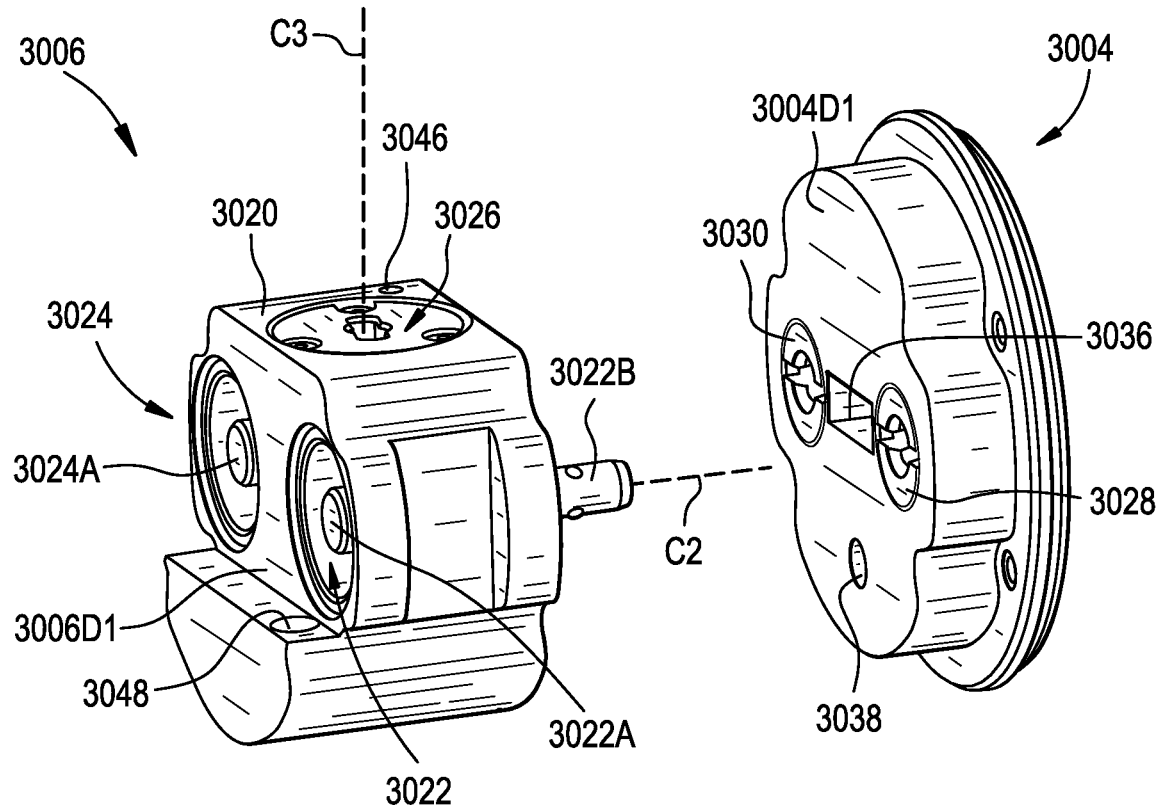
FIG. 39 illustrates a step in one embodiment of coupling the sterile connector of FIG. 38 to the robot plate of FIG. 38.
Figure 40:
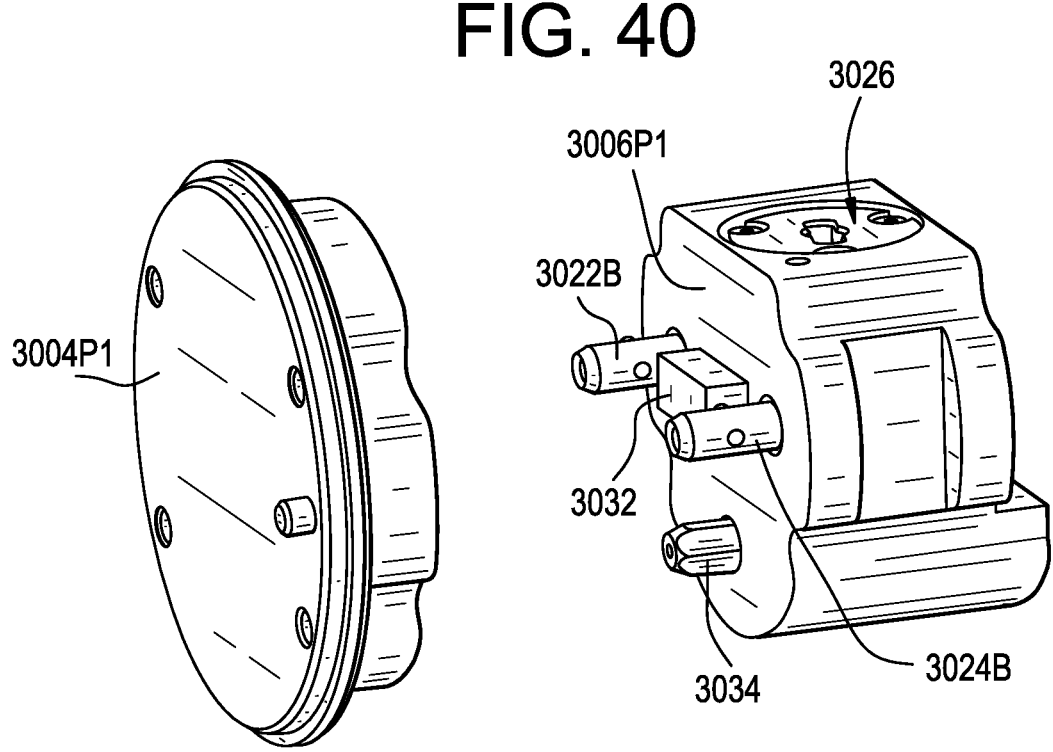
FIG. 40 illustrates the step shown in FIG. 39 from another perspective.

FIGS. 39 and 40 illustrate coupling the sterile connector 3004 axially to the robot plate 3004. The sterile connector 3004 can be moved along an axis parallel to the central longitudinal axis C1 such that first pin locking shaft 3022B can be received within the first pin lock receptacle 3028, and the second pin locking shaft 3024B can be received within the second pin lock receptacle 3030. In some embodiments, the ball-lock pins 3022, 3024 can be self-locking such that the ball-lock pin locking shafts 3022B, 3024B can lock within the lock receptacles 3028, 3030 upon insertion. Accordingly, the sterile connector 3006 can be locked to the robot plate 3004 when the ball-lock pin shafts 3022B, 3024B are fully received within the receptacles 3028, 3030. The sterile connector 3006 can have additional alignment features, such as extension 3032 and dowel pin 3034, that can extend proximally from the proximal facing surface 3006P1. The extension 3032 and dowel pin 3034 can be received within counterpart recesses 3036, 3038 that can be formed in the distal facing surface 3004D1 of the robot plate 3004. In some embodiments, a force can be applied to depress the pin head 3022A, 3024A, which can move the ball-lock pin clamp 3022, 3024 from a locked position within the pin lock receptacle 3028, 3030 to an unlocked position. When in the unlocked position, the ball-lock pin clamps 3022, 3030, and, accordingly, the sterile connector 3006 can be separated from the pin clamp receptacles 3028, 3030 and the robot plate 3004.

Figure 41:
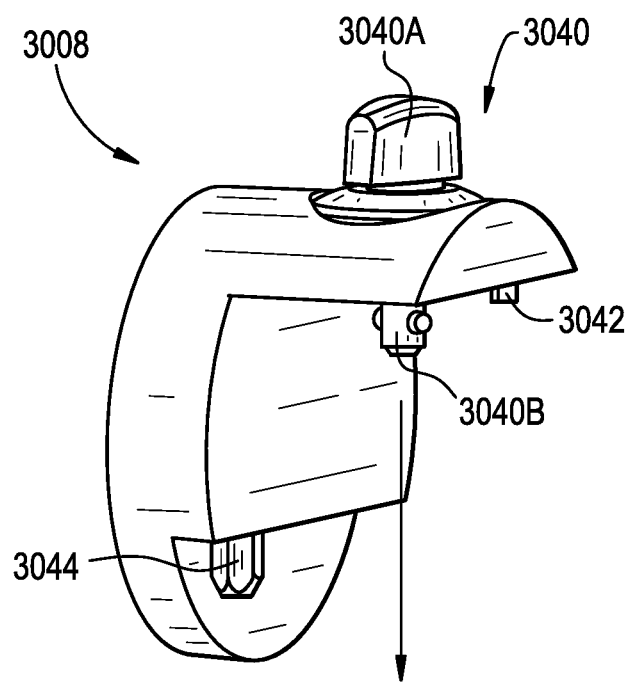
FIG. 41 illustrates a step in one embodiment of coupling the end effector of FIG. 38 to the sterile connector of FIG. 38.
Figure 41:
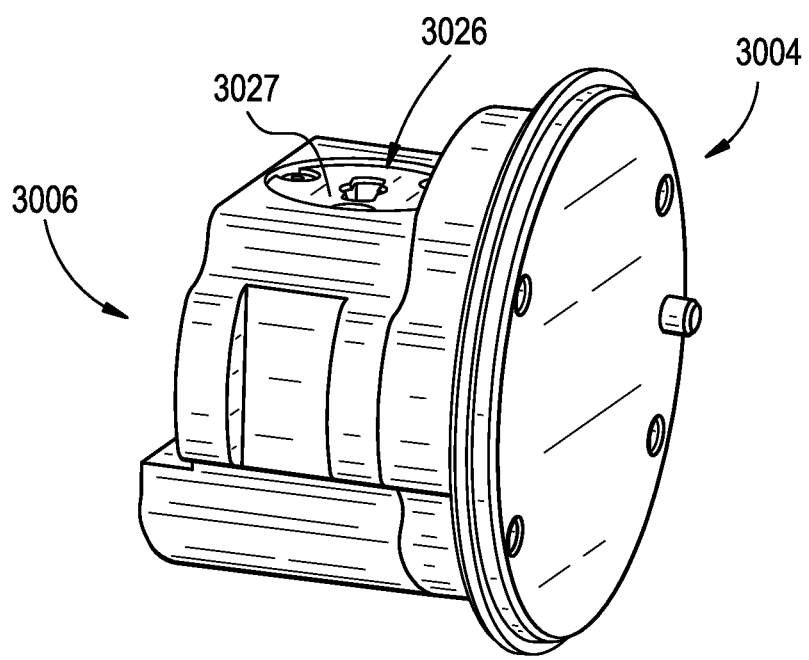

FIG. 41 illustrates radial coupling of the end effector 3008 with the sterile connector 3006, which can occur in a similar manner as described above. An end effector component connector 3040 can include a lock, such as a quarter-turn lock, that can extend radially through the end effector 3008.

A locking shaft 3040B of the lock 3040 can be inserted into the sterile connector's third component connector 3026, e.g., a lock receptacle 3027. The lock 3040 can be moved from an unlocked position to a locked position, which can lock the end effector 3008 to the sterile connector 3006. The end effector can have dowel pins 3042, 3044 that can be received within complementary recesses 3046, 3048 within the body 3020 of the sterile connector 3006 when the end effector 3008 is coupled with the sterile connector 3006. The end effector 3008 can be coupled to the sterile connector 3006 and can cover the pin heads 3022A, 3024A such that the pin heads cannot be accessed. Accordingly, the ball-lock pins 3022, 3024 can be prevented from being moved from the locked position to the unlocked position while the end effector 3008 is coupled to the sterile connector 3006.

Although specific embodiments are described above, changes may be made within the spirit and scope of the concepts described. For example, a sterile connector, an end effector, and/or a robot plate may include one or more signal connectors configured to transmit electrical signals and one or more signal connectors configured to transmit light. In some embodiments a signal connector can transmit both electrical signals and light. Accordingly, it is intended that this disclosure not be limited to the described embodiments, but that it have the full scope defined by the language of the claims. All publications and references cited herein are expressly incorporated herein by reference in their entirety.

The invention claimed is:

1. A surgical system comprising:
a connector for connecting an end effector to a surgical robot arm, the connector comprising:
a first part for engaging the robot arm in a first axis;
a second part for engaging the end effector in a second axis, wherein the first axis and the second axis are transverse relative to one another, and wherein, when the end effector engages the second part, the first part is prevented from disengaging from the robot arm; and
a user interface including one or more visual indicators; and
a sterile conductive drape attached to the connector, wherein the first part and second part cooperate to retain the drape interposed between the first part and second part to create a sterile barrier between the robot arm and the end effector.

2. The system of claim 1, wherein the drape comprises a conductive coating or a conductive thread and wherein electrical signals are passed through the drape to notify a user when the sterile barrier is broken.

3. The system of claim 2, wherein the one or more visual indicators are displayed when the sterile barrier is broken.

4. The system of claim 1, wherein the one or more visual indicators are displayed when the connector is in a locked position.

5. The system of claim 1, wherein the connector further comprises a signal connector.

6. The system of claim 5, wherein the signal connector is configured to transmit electrical signals to at least one of the robot arm or the end effector.

7. The system of claim 6, wherein the signal connector is configured to transmit light signals to at least one of the robot arm or the end effector.

8. The system of claim 1, wherein the first part further comprises a first lock.

9. The system of claim 8, wherein the second part further comprises a second lock.

10. The system of claim 1, wherein the end effector and the second part further have cooperating pins and recesses to align the end effector and the second part.

11. The system of claim 1, wherein the connector further comprises a communication bus to pass electrical signals from the robot arm to the end effector via the connector.

12. A surgical system comprising:
a surgical robot arm;
an end effector; and
a connector interposed between the robot arm and the end effector for connecting the end effector to the robot arm, wherein a first portion of the connector engages the robot arm in a first axis and a second portion of the connector engages the end effector in a second axis, wherein the first axis and the second axis are transverse relative to one another, and wherein, when the second portion of the connector engages the end effector, the first portion is prevented from disengaging from the robot arm.

13. The system of claim 12, wherein the second axis is substantially the same as an intended insertion trajectory of a surgical instrument into the end effector.

14. The system of claim 12, wherein the connector further comprises a user interface including one or more visual indicators, wherein at least one visual indicator is displayed when the connector is locked to the robot arm.

15. The system of claim 12, wherein the first portion includes a first lock movable between a first position that locks the first portion to the robot arm and a second position that permits separation of the first portion from the robot arm.

16. The system of claim 15, wherein the first lock cannot be moved from the first position to the second position when the second portion engages the end effector.

17. The system of claim 15, wherein the first lock is blocked from movement from the first position by the end effector.

18. The system of claim 12, wherein the second portion includes a second lock movable between a first position that locks the second portion to the end effector and a second position that permits separation of the second portion from the end effector.

19. The system of claim 18, wherein the second lock is substantially aligned with the second axis.

20. The system of claim 18, wherein when the first lock and the second lock are in their respective first positions, the connector is adapted to transmit electrical signals between the robot arm and the end effector.

* * * * *